(12) United States Patent
Takai et al.

(10) Patent No.: US 8,115,043 B2
(45) Date of Patent: Feb. 14, 2012

(54) METHOD FOR PRODUCING CYCLIC OLEFIN COMPOUND

(75) Inventors: Hideyuki Takai, Ohtake (JP); Kenji Oka, Ohtake (JP); Kyuhei Kitao, Ohtake (JP)

(73) Assignee: Daicel Chemical Industries, Ltd., Osaka-shi (JP)

( * ) Notice: Subject to any disclaimer, the term of this patent is extended or adjusted under 35 U.S.C. 154(b) by 645 days.

(21) Appl. No.: 12/226,356

(22) PCT Filed: Apr. 11, 2007

(86) PCT No.: PCT/JP2007/057966
§ 371 (c)(1),
(2), (4) Date: Oct. 16, 2008

(87) PCT Pub. No.: WO2007/119743
PCT Pub. Date: Oct. 25, 2007

(65) Prior Publication Data
US 2009/0062580 A1 Mar. 5, 2009

(30) Foreign Application Priority Data

Apr. 18, 2006 (JP) .................................. 2006-114790
Apr. 6, 2007 (JP) .................................. 2007-100390

(51) Int. Cl.
*C07C 1/20* (2006.01)
(52) U.S. Cl. ....................................... 585/639; 585/638
(58) Field of Classification Search .................... None
See application file for complete search history.

(56) References Cited

U.S. PATENT DOCUMENTS
2003/0059618 A1 3/2003 Takai

FOREIGN PATENT DOCUMENTS

| JP | 2000-169399 A | 6/2000 |
|---|---|---|
| JP | 2002-275169 A | 9/2002 |
| JP | 2002-338659 A | 11/2002 |
| JP | 2004-285125 A | 10/2004 |
| JP | 2004-346007 A | 12/2004 |
| JP | 2005-97274 A | 4/2005 |
| JP | 2006-36862 A | 2/2006 |
| JP | 2006-96701 A | 4/2006 |

OTHER PUBLICATIONS

Blatt, ed., Organic Syntheses, vol. 2, pp. 151-153, 1943.
Cahn et al., eds., Journal of the Chemical Society, Part III, pp. 1975-2914, 1950.
Shin Jikken Kagaku Koza, Syntheses and Reactions of Organic Compounds, vol. 14, pp. 119, 1978.
Notification from Japanese Patent Office dated Nov. 9, 2010 of a Submission by Third Party filed on Oct. 29, 2010 in the Japanese Patent Office for corresponding Japanese Application No. 2008-510964.

*Primary Examiner* — Tam M Nguyen
(74) *Attorney, Agent, or Firm* — Birch, Stewart, Kolasch & Birch, LLP

(57) ABSTRACT

Disclosed is a method for producing a cyclic olefin compound having two or more cyclohexene rings per molecule via intramolecular dehydration of an alicyclic alcohol having two or more hydroxylated cyclohexane rings per molecule. The method includes the step (i) of heating the alicyclic alcohol at a temperature of 130° C. to 230° C. and a pressure greater than 20 Torr in an organic solvent in the presence of a dehydration catalyst, to carry out dehydration of the alicyclic alcohol while distilling off by-product water, which dehydration catalyst is liquid or soluble in a liquid reaction mixture under the reaction conditions; and the subsequent step (ii) of heating the resulting reaction mixture at a temperature of 50° C. to 220° C. and a pressure of 200 Torr or less to recover the cyclic olefin compound as a distillate. According to the method, side reactions such as isomerization are suppressed, and high-purity cyclic olefin compounds with less impurities can be simply and efficiently obtained in high yields.

8 Claims, 10 Drawing Sheets

[Fig. 1]
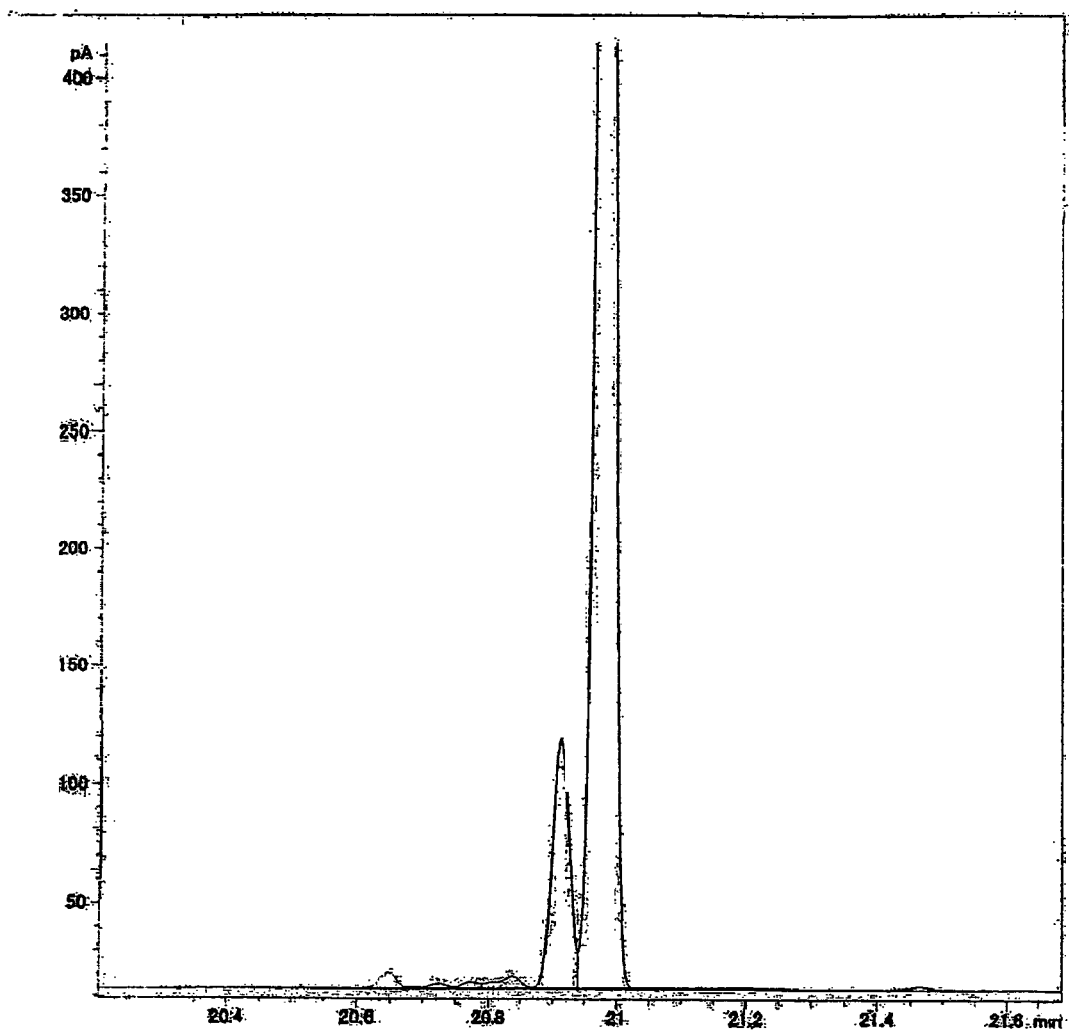

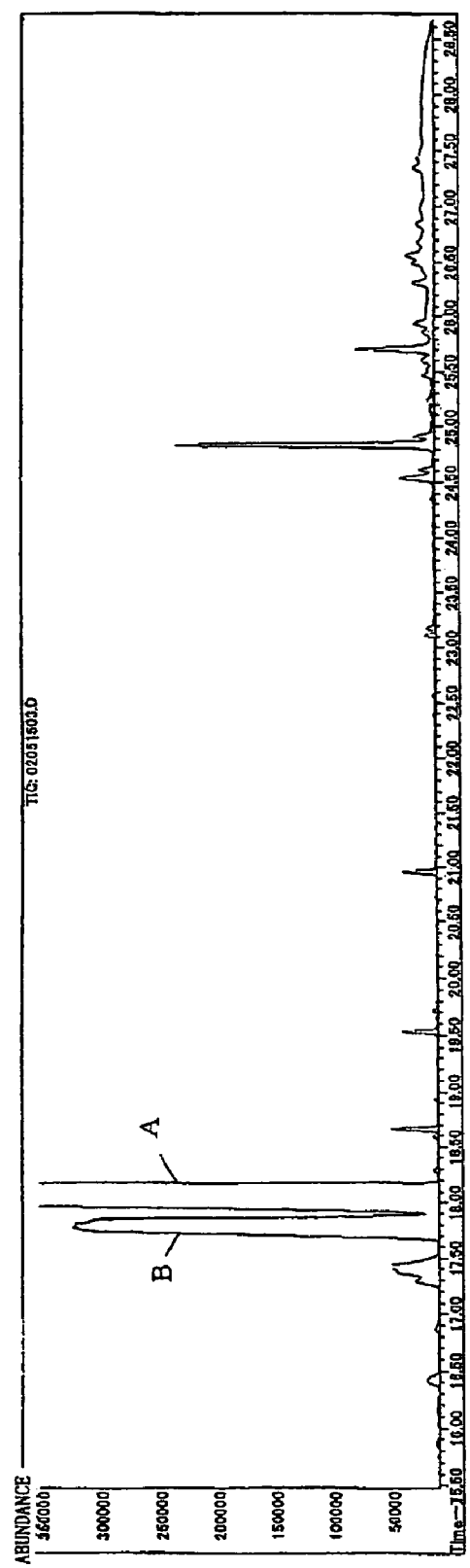
[Fig. 2]

[Fig. 3]
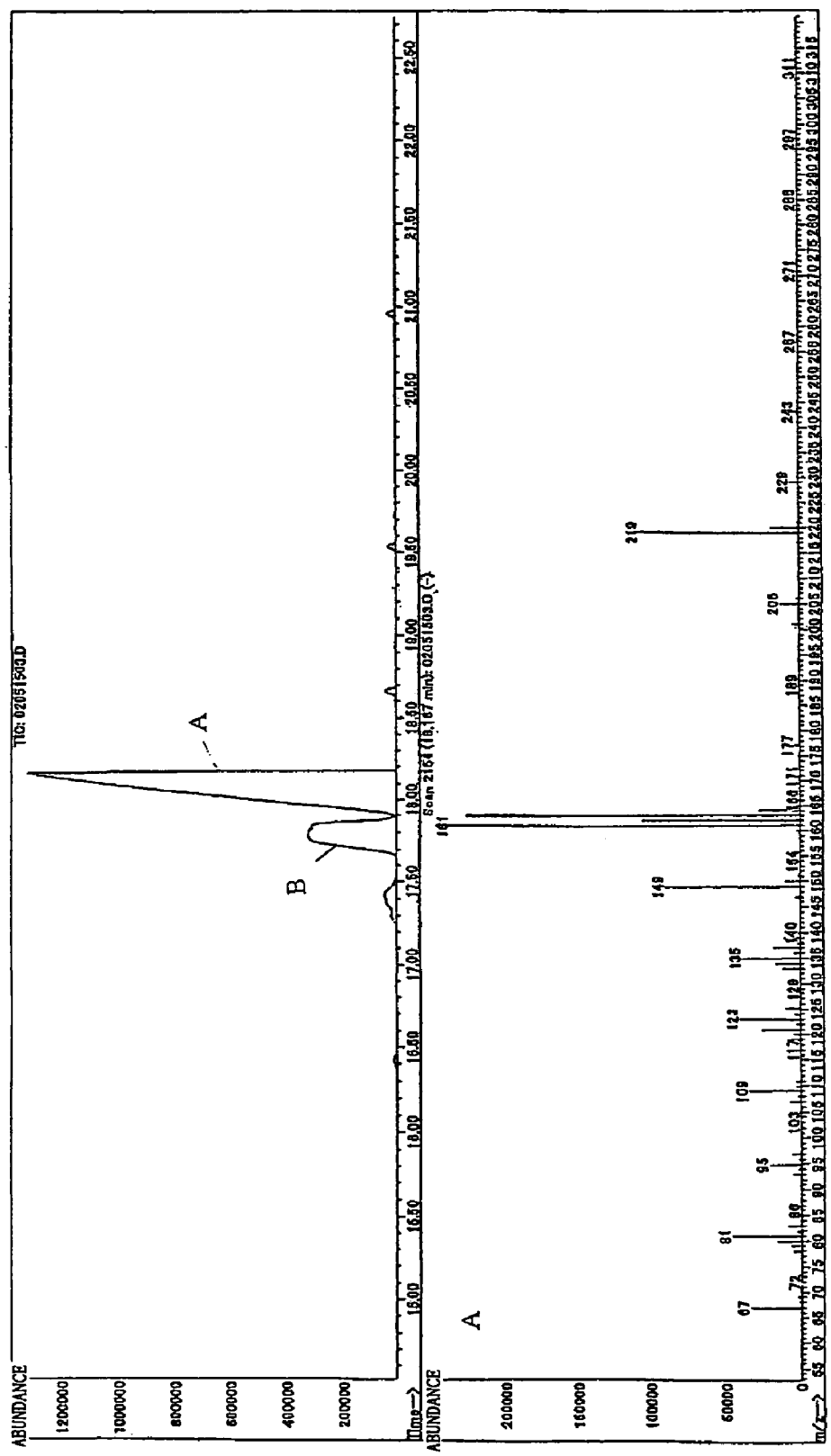

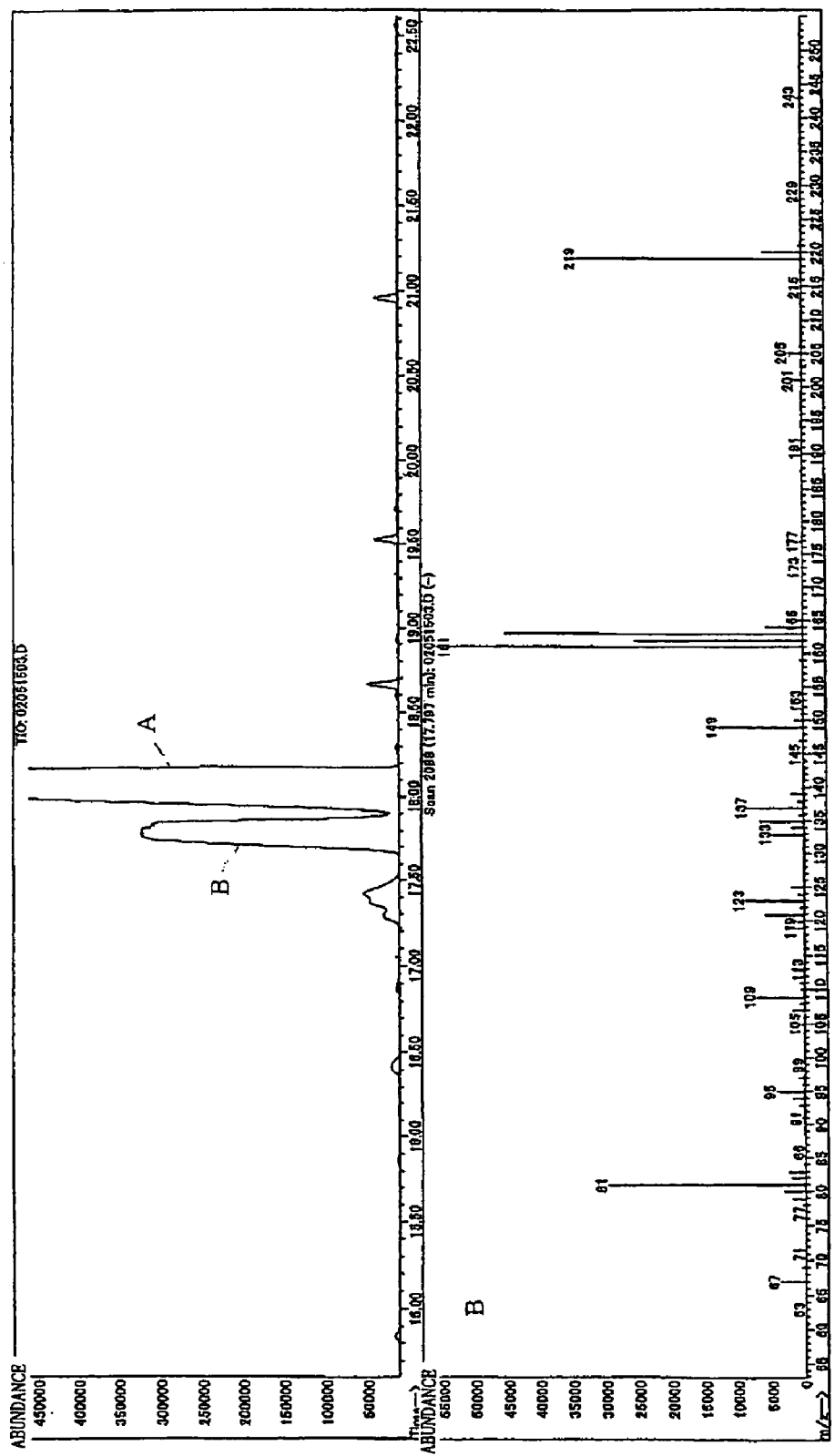
[Fig. 4]

[Fig. 5]
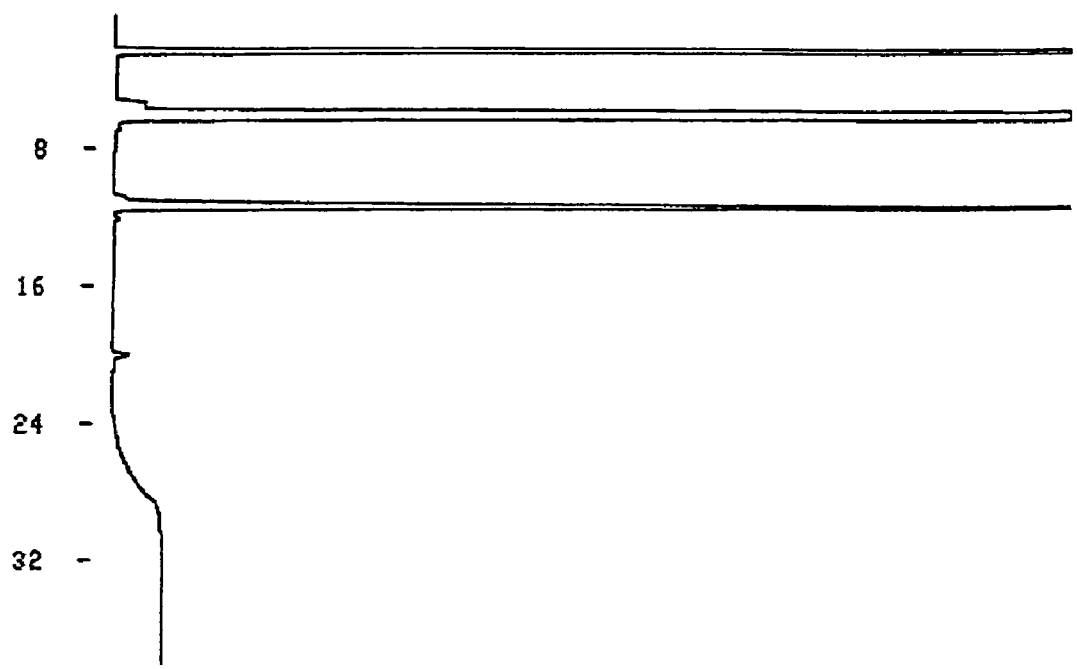

[Fig. 6]
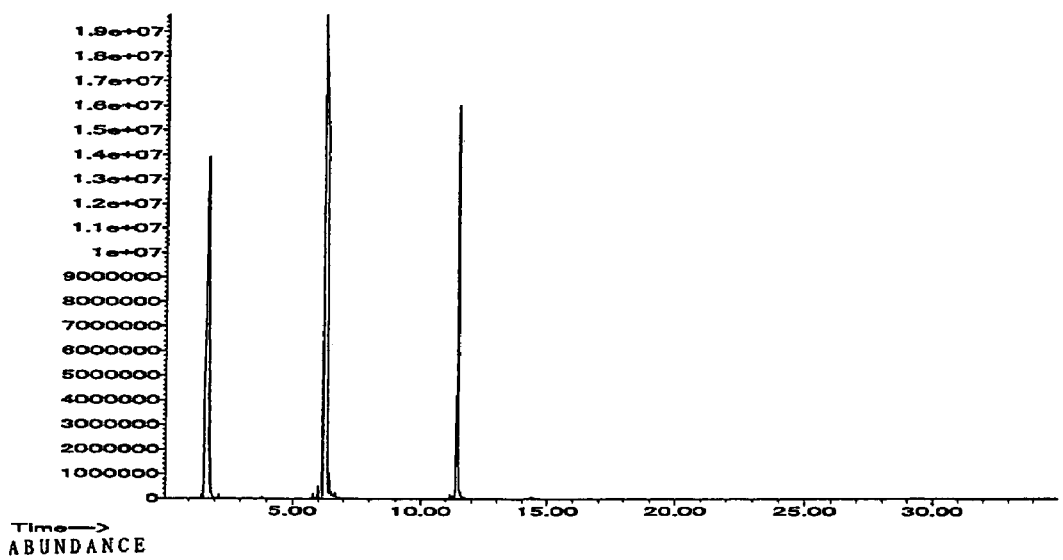
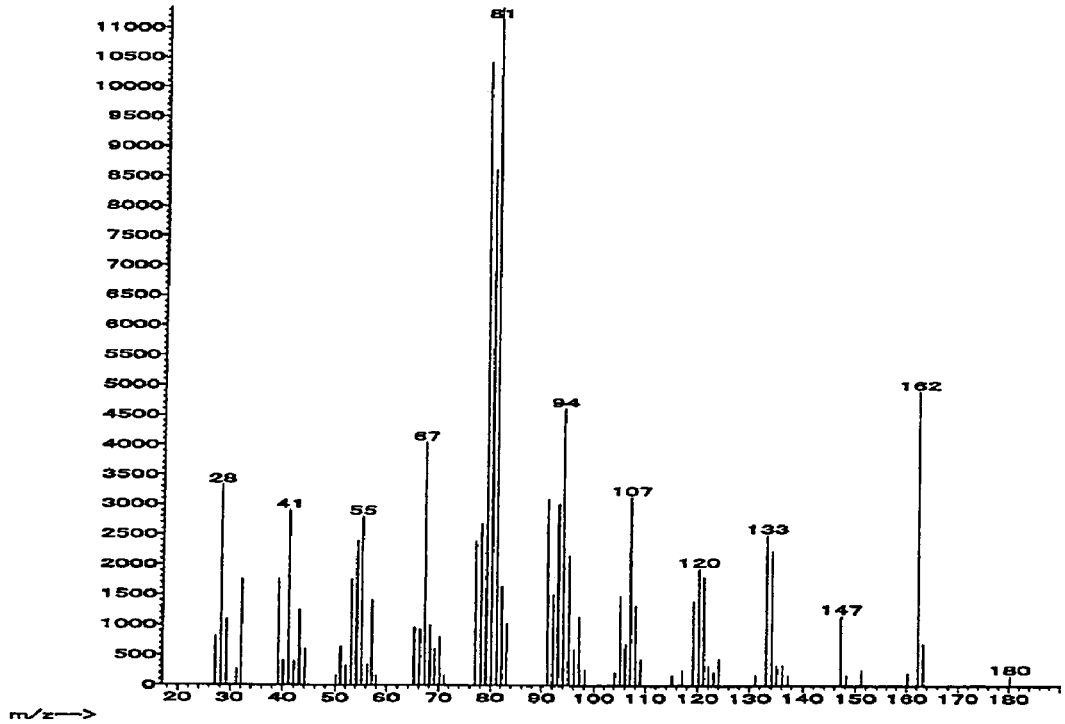

[Fig. 7]
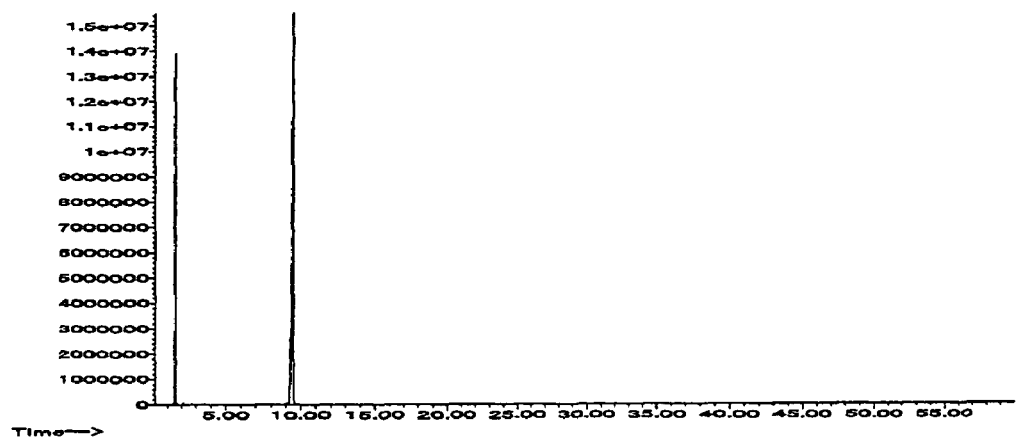
[Fig. 8]
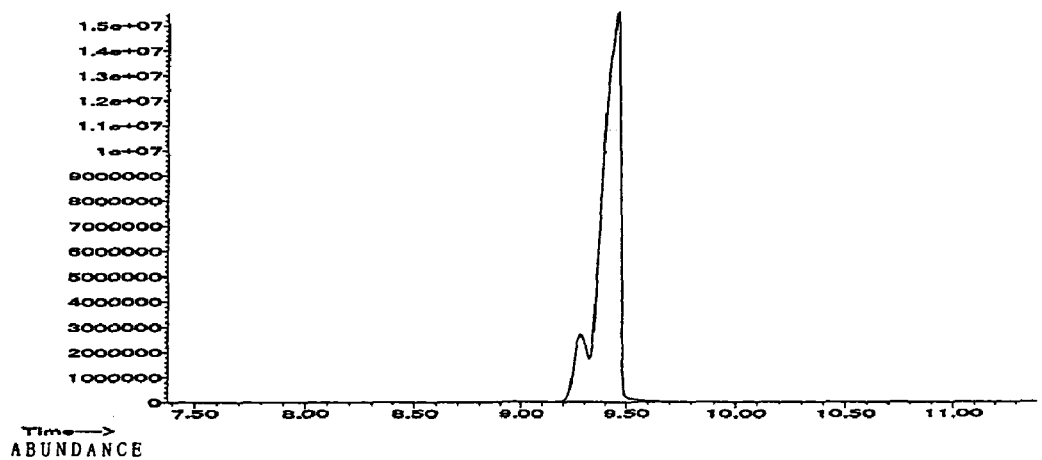
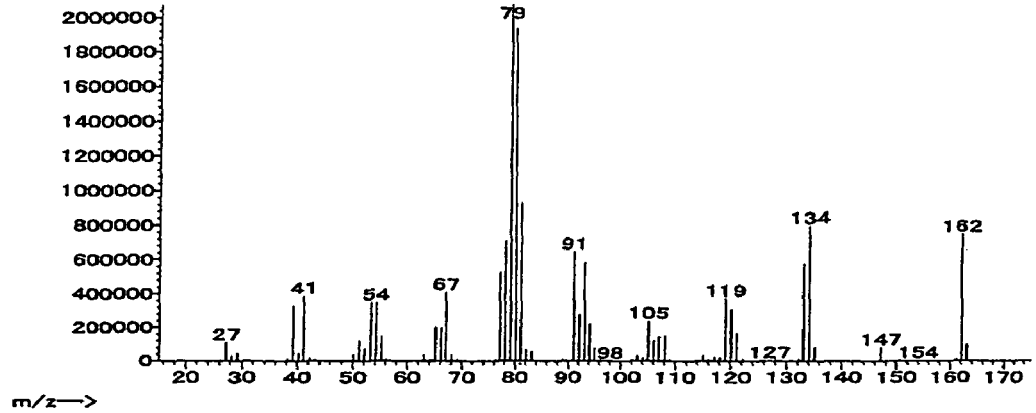

[Fig. 9]
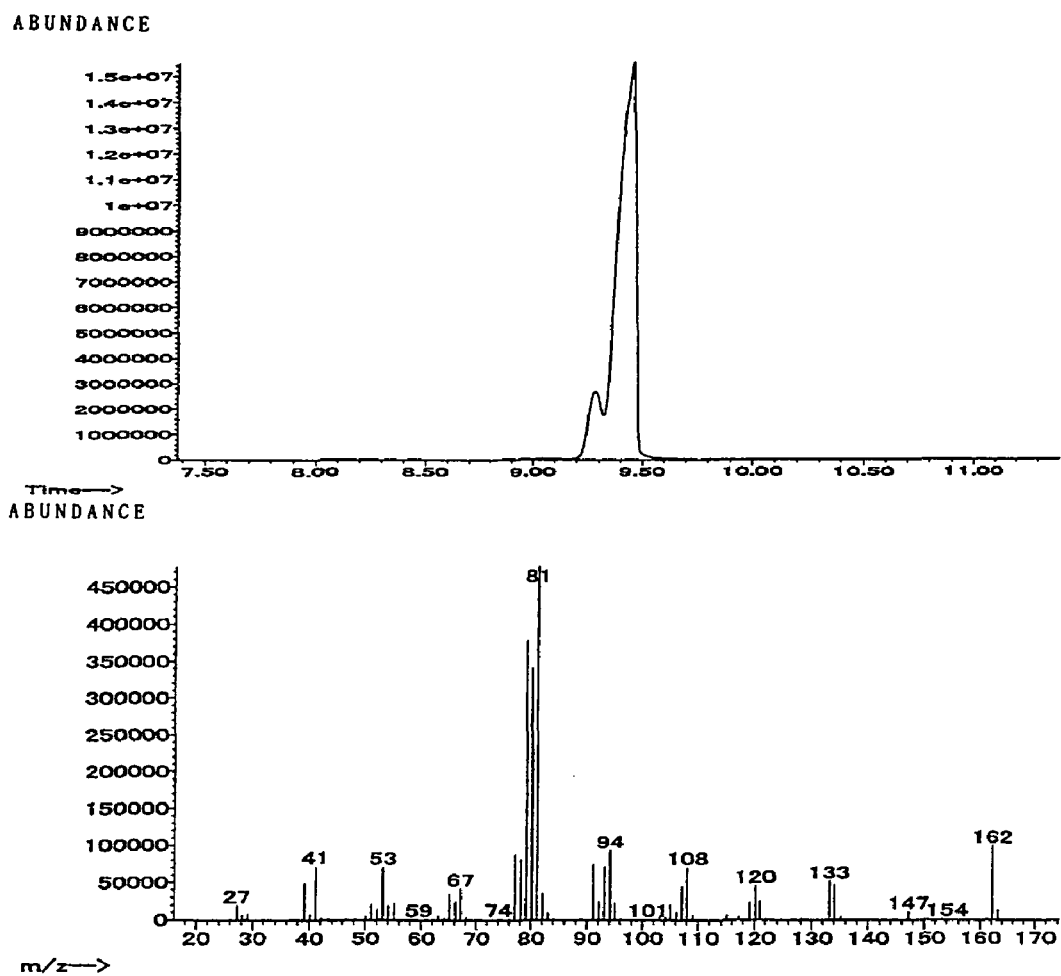

[Fig. 10]
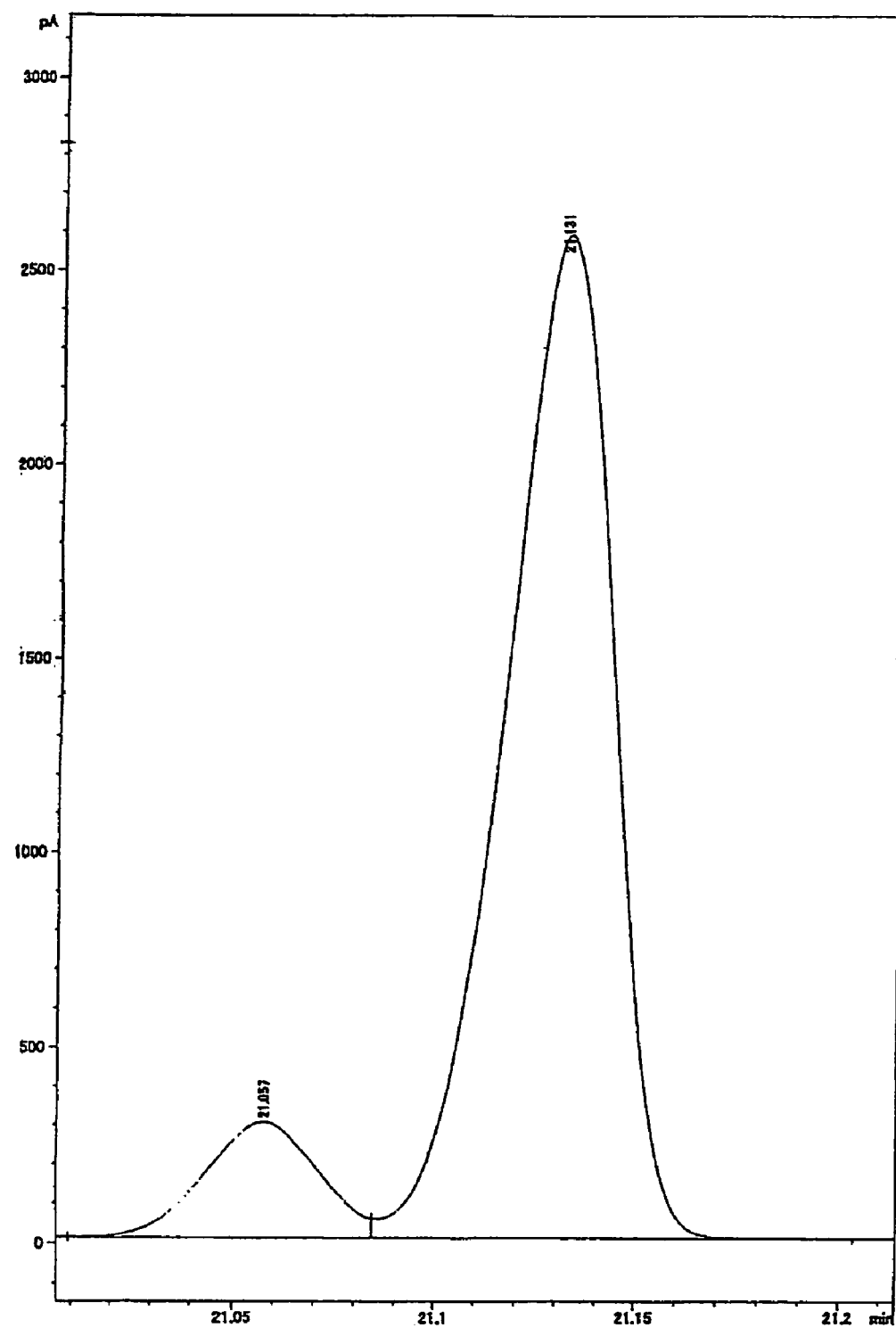

[Fig. 11]
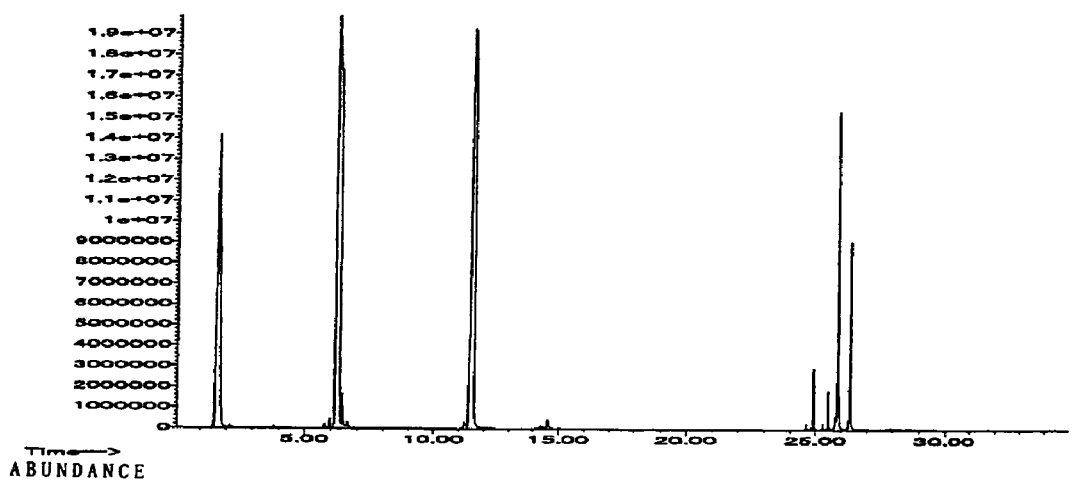
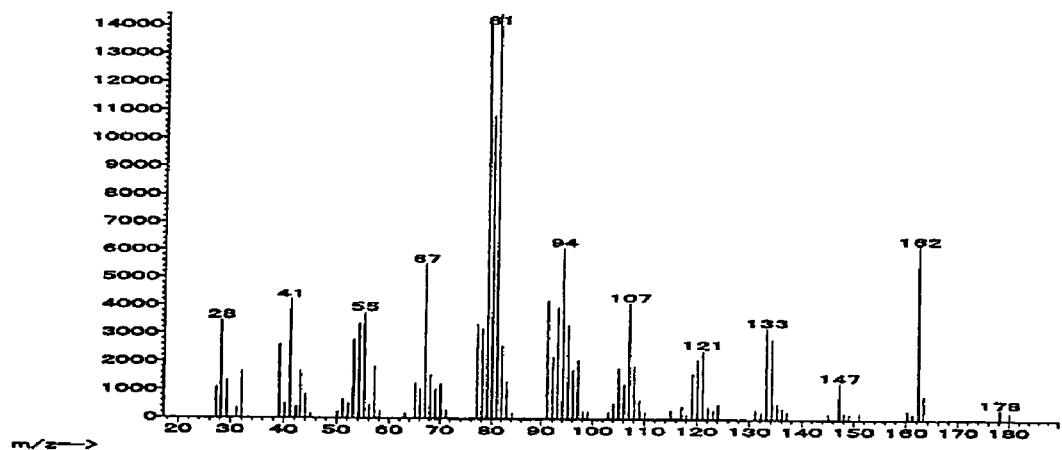

METHOD FOR PRODUCING CYCLIC OLEFIN COMPOUND

TECHNICAL FIELD

The present invention relates to methods for producing cyclic olefin compounds. More specifically, it relates to methods for producing cyclic olefin compounds each having two or more cyclohexene rings per molecule from alicyclic alcohols each having two or more hydroxylated cyclohexane rings per molecule and to high-purity cyclic olefin compounds produced by the methods.

BACKGROUND ART

In well known methods, cyclic olefin compounds each having a cyclohexene skeleton are produced via dehydration of alcohols. Typically, there are disclosed in documents a technique of producing a cyclic olefin compound via dehydration of an alcohol by the catalysis of an inorganic acid such as a concentrated sulfuric acid or phosphoric acid (see Non-patent Document 1) and techniques for producing cyclic olefin compounds via dehydration of alcohols using potassium hydrogen sulfate ($KHSO_4$) as an acidic salt (see Patent Document 1, Non-patent Document 2, and Non-patent Document 3).

These known techniques for producing cyclic olefin compounds, however, are not always satisfactory in yield and purity of the resulting cyclic olefin compounds. Specifically, the known technique using a concentrated sulfuric acid with high acidity is likely to suffer from side reactions, and the resulting by-product compounds other than a target cyclic olefin compound reduce the yield of the target cyclic olefin compound. In the other known techniques using an inorganic salt of sulfuric acid, such as potassium hydrogen sulfate, or phosphoric acid, the reaction should be carried out at a higher temperature and/or for a longer duration, because these components have low acidity. Consequently, side reactions also occur to reduce the yield of the target cyclic olefin compound and to cause by-product colored components and isomer components which are very hard to be separated from the target cyclic olefin compound. In addition, an inorganic salt of sulfuric acid, such as potassium hydrogen sulfate, is very sparingly soluble in reaction materials and organic solvents, whereby the reaction should be carried out at a further higher temperature for a further longer duration, and this causes considerable side reactions. Additionally, in the known techniques, the concentration of substrate is generally low and the reducibility is considerably low.

Particularly in production of a cyclic olefin compound having two or more cyclohexene rings per molecule via intramolecular dehydration of an alicyclic alcohol having two or more hydroxylated cyclohexane rings per molecule, isomerization occurs during the reaction to form by-product isomers differing in the position of double bond and to form by-product cyclic olefin compounds in which, for example, only one of hydroxylated cyclohexane rings has been dehydrated (i.e., cyclic olefin compounds each having one or more residual hydroxylated cyclohexane rings per molecule). These isomers have properties, such as boiling point and solubility in an solvent, similar to those of the target compound, and when once formed, they are difficult to separate from the target compound and contaminate the product, thus, it is difficult to obtain the target compound with a high purity. Additionally, some of cyclic olefin compounds having one or more residual hydroxylated cyclohexane rings per molecule are sublimable and may adhere to walls of a reactor and attachments thereof to cause a blockage of the system.

This will be illustrated in further detail. By way of example, when a cyclohexyl alcohol derivative having a substituent at the 4-position is heated in the presence of a dehydration catalyst, and when the heating is conducted in a system in the coexistence of water, not only dehydration but also reverse reactions thereof (addition reactions of water) proceed to form, in addition to a target cyclic olefin, by-product two isomers differing in the position of double bond as illustrated in the following reaction formula in which R represents a substituent.

[Chemical Formula 7]

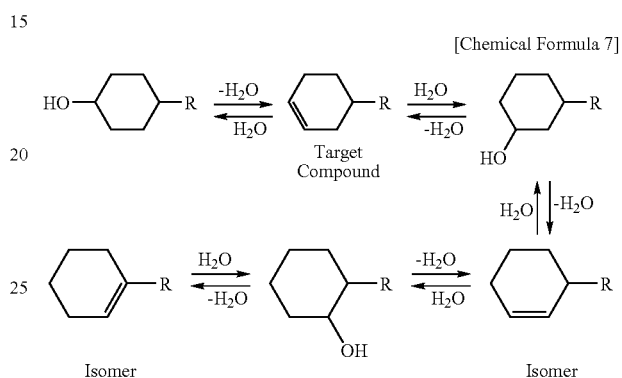

In addition, the number of isomers further increases when the substituent R has one or more hydroxylated cyclohexane rings. By way of example, when a hydrogenated biphenol represented by following Formula (1a):

[Chemical Formula 8]

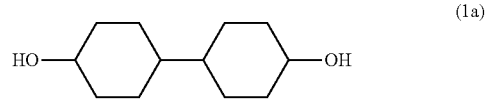

(1a)

is used as a starting material, six different isomers (cyclic olefin compounds) represented by following Formulae (3a) to (3f) can be formed. Specifically, five different by-products can be formed when a compound represented by Formula (3a) (bicyclohexyl-3,3'-diene; a colorless transparent liquid having a boiling point of 260° C. at 760 Torr and 140° C. at 10 Torr) is the target compound.

[Chemical Formula 9]

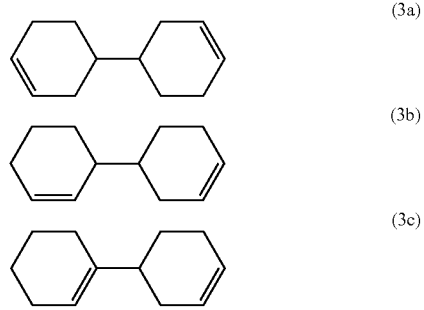

(3a)

(3b)

(3c)

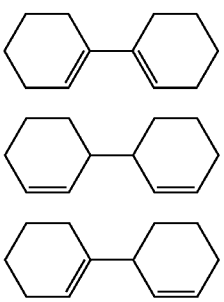

(3d)

(3e)

(3f)

Dehydration of a cyclohexyl alcohol derivative having two or more hydroxylated cyclohexane rings per molecule may yield a reaction intermediate having a cyclohexene ring and a hydroxylated cyclohexane ring per molecule. Typically, dehydration of the hydrogenated biphenol as a starting material gives a by-product compound represented by following Formula (4) (a white solid (at normal temperature) having a boiling point of 380° C. at 760 Torr and 230° C. at 10 Torr). This compound is sublimable and may adhere to the inside typically of a distillation column, if provided in a reactor, and may cause a blockage of the distillation column.

[Chemical Formula 10]

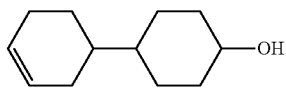

(4)

On the other hand, Japanese Unexamined Patent Application Publication (JP-A) No. 2005-97274 (Patent Document 2) discloses a method of producing bicyclohexyl-3,3'-diene via intramolecular dehydration of hydrogenated biphenol in the presence of an alkali metal hydrogen sulfate such as potassium hydrogen sulfate and in the absence of a solvent, in which produced water and bicyclohexyl-3,3'-diene are immediately distilled off from the reactor to prevent side reactions and to thereby give high-purity bicyclohexyl-3,3'-diene. According to this method, however, it is difficult to render the reaction system homogeneous even at temperatures at which a reaction begins, because the starting material hydrogenated biphenol melts at around 180° C., and it is difficult to stir the reaction system until the temperature rises to around this temperature. Additionally, use of potassium hydrogen sulfate requires a corrosion-resisting apparatus typically with glass lining, because potassium hydrogen sulfate corrodes stainless steels SUS 304 and SUS 316 which are generally used as materials for chemical apparatuses (chemical plants) made of metals. However, there are few glass-lined reactors that can be heated up to such high temperatures of from 180° C. to 200° C. In addition, heat shock due to produced water may probably cause a crack or delamination of the glass lining. Thus, this method is highly susceptible to improvements in order to carry out industrially. Furthermore, the method requires a large amount of a dehydration catalyst.

[Patent Document 1] JP-A No. 2000-169399
[Patent Document 2] JP-A No. 2005-97274
[Non-patent Document 1] Org. Synth. Coll. Vol. 2, 151 (1943)
[Non-patent Document 2] J. Chem. Soc., 1950, 2725
[Non-patent Document 3] Shin Jikken Kagaku Koza (in Japanese; "Courses in Experimental Chemistry, New Ed.") vol. 14, Syntheses and Reactions of Organic Compounds I, 119 (1978) edited by The Chemical Society of Japan

DISCLOSURE OF INVENTION

Problems to be Solved by the Invention

Accordingly, an object of the present invention is to provide a method for producing a cyclic olefin compound, which method suppresses side reactions such as isomerization and simply and efficiently yields a high-purity cyclic olefin compound with less impurities in a high yield. Another object of the present invention is to provide a method for producing a cyclic olefin compound, which method requires only a small amount of catalyst, allows a reaction to proceed at relatively low temperatures within a relatively short period, is satisfactorily easy to operate, does not require any apparatuses made of special materials, and is suitable for industrial production. Yet another object of the present invention is to provide a method for producing a cyclic olefin compound, which method further noticeably suppresses by-production of high-boiling impurities. Still another object of the present invention is to provide a cyclic olefin compound containing, if any, very small amounts of isomers.

Means for Solving the Problems

After intensive investigations to achieve the objects, the present inventors have found that side reactions such as isomerization are suppressed and a high-purity cyclic olefin compound containing less impurities can be simply and efficiently produced in a high yield upon production of a cyclic olefin compound having two or more cyclohexene rings per molecule via dehydration of an alicyclic alcohol having two or more hydroxylated cyclohexane rings per molecule, by reacting the alicyclic alcohol in an organic solvent in the presence of a specific dehydration catalyst under specific conditions and subsequently carrying out distillation under specific conditions to recover the resulting cyclic olefin compound as a distillate.

Specifically, the present invention provides a method for producing a cyclic olefin compound having two or more cyclohexene rings per molecule via intramolecular dehydration of an alicyclic alcohol having two or more hydroxylated cyclohexane rings per molecule. The method includes the step (i) of heating the alicyclic alcohol at a temperature of from 130° C. to 230° C. and a pressure greater than 20 Torr (2.67 kPa) in an organic solvent in the presence of a dehydration catalyst to carry out dehydration of the alicyclic alcohol while distilling off by-product water, the dehydration catalyst being liquid or soluble in a liquid reaction mixture under the reaction conditions; and the subsequent step (ii) of heating the resulting reaction mixture at a temperature of from 50° C. to 220° C. and a pressure of 200 Torr (26.7 kPa) or less to recover the cyclic olefin compound as a distillate.

The dehydration in the step (i) may be carried out by intermittently or continuously adding the alicyclic alcohol to the organic solvent at a pressure greater than 20 Torr kPa) while distilling off by-product water, in which the organic solvent is heated at a temperature of from 130° C. to 230° C. and is coexistent with the dehydration catalyst that is liquid or soluble in a liquid reaction mixture under the reaction conditions.

The method for producing a cyclic olefin compound may include carrying out intramolecular dehydration of an alicyclic alcohol represented by following Formula (1):

[Chemical Formula 11]

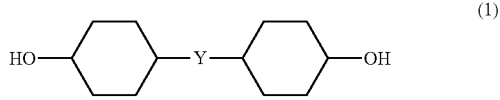

(1)

wherein Y represents a bivalent group selected from the group consisting of single bond, oxygen atom, sulfur atom, —SO—, —SO$_2$—, and a halogenated or unhalogenated bivalent hydrocarbon group having a linear, branched, or cyclic skeleton and containing one to eighteen carbon atoms, or a bivalent group composed of two or more of these groups bonded with each other,
to yield a cyclic olefin compound represented by following Formula (2):

[Chemical Formula 12]

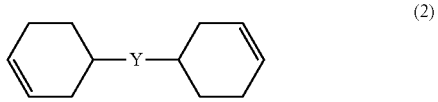

(2)

wherein Y is as defined above.

The organic solvent may be at least one solvent selected from aromatic hydrocarbons and aliphatic hydrocarbons.

The dehydration catalyst that is liquid or soluble in a liquid reaction mixture under the reaction conditions may be at least one selected from the group consisting of a sulfonic acid, phosphoric acid, sulfuric acid, a fully neutralized salt of a sulfonic acid with an organic base, a fully neutralized salt of phosphoric acid with an organic base, a fully neutralized salt of sulfuric acid with an organic base, a partially neutralized salt of a sulfonic acid with an organic base, a partially neutralized salt of phosphoric acid with an organic base, and a partially neutralized salt of sulfuric acid with an organic base.

The dehydration catalyst that is liquid or soluble in a liquid reaction mixture under the reaction conditions may be used in an amount of, for example, about 0.001 to about 0.5 mole per 1 mole of the alicyclic alcohol.

Exemplary alicyclic alcohols each having two or more hydroxylated cyclohexane rings per molecule include a compound represented by following Formula (1a):

[Chemical Formula 13]

(1a)

a compound represented by following Formula (1b):

[Chemical Formula 14]

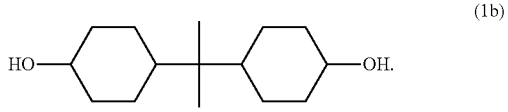

(1b)

and a compound represented by following Formula (1c):

[Chemical Formula 15]

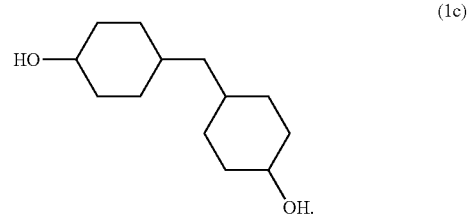

(1c)

The present invention further provides a cyclic olefin compound produced by the method.

The present invention also provides a cyclic olefin compound as a mixture of isomers of a cyclic olefin compound having two or more cyclohexene rings per molecule, in which the ratio of a major compound to isomers thereof (total of isomers differing in the position of double bond from the major compound) is from 81.5:18.5 to 99:1 in terms of an area ratio determined by gas chromatography.

In addition, the present invention provides a cyclic olefin compound as a mixture of a cyclic olefin compound represented by following Formula (2):

[Chemical Formula 16]

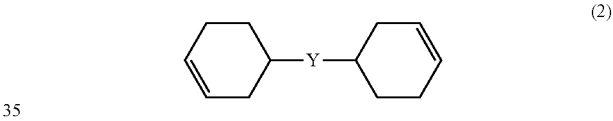

(2)

wherein Y represents a bivalent group selected from the group consisting of single bond, oxygen atom, sulfur atom, —SO—, —SO$_2$—, and a halogenated or unhalogenated bivalent hydrocarbon group having a linear, branched, or cyclic skeleton and containing one to eighteen carbon atoms, or a bivalent group composed of two or more of these groups bonded with each other,
with isomers thereof differing in the position of double bond from the cyclic olefin compound, in which the ratio of the cyclic olefin compound to the isomers is from 81.5:18.5 to 99:1 in terms of an area ratio determined by gas chromatography.

Advantages

According to the present invention, side reactions such as isomerization can be suppressed, to yield high-purity cyclic olefin compounds containing less impurities simply in high yields. The production method according to the present invention requires only a small amount of catalyst, allows a reaction to proceed at relatively low temperatures within a relatively short period, is easy to operate, does not require any apparatuses made of special materials, and is suitable for industrial production. Particularly when the dehydration is carried out while intermittently or continuously adding an alicyclic alcohol into an organic solvent including a dehydration catalyst, by-production of high-boiling impurities can be noticeably suppressed to thereby improve the yield of a target compound significantly. In addition, the present invention provides cyclic olefin compounds containing, if any, very small amounts of isomers.

BRIEF DESCRIPTION OF DRAWINGS

FIG. 1 depicts a chart in gas chromatography of bicyclohexyl-3,3'-diene (including isomers) obtained in Example 2.

FIG. 2 depicts a total ion chromatogram of a liquid (distillate) obtained in Comparative Example 3 as determined through gas chromatography-mass spectrometry (GC/MS).

FIG. 3 depicts a total ion chromatogram of the liquid (distillate) obtained in Comparative Example 3 (upper chart); and a mass spectrometric chart of the target compound (lower chart), as determined through gas chromatography-mass spectrometry (GC/MS).

FIG. 4 depicts a total ion chromatogram of the liquid (distillate) obtained in Comparative Example 3 (upper chart); and a mass spectrometric chart of isomers (lower chart), as determined through gas chromatography-mass spectrometry (GC/MS).

FIG. 5 depicts a gas chromatographic chart of a solution obtained after the completion of dehydration in Example 10.

FIG. 6 depicts a total ion chromatogram of the solution obtained after the completion of dehydration in Example 10 (upper chart); and a mass spectrometric chart of 4-(3'-cyclohexenyl)cyclohexanol as a reaction intermediate (lower chart), as determined through gas chromatography-mass spectrometry (GC/MS).

FIG. 7 depicts a total ion chromatogram of a liquid (distillate) obtained in Example 10, as determined through gas chromatography-mass spectrometry (GC/MS).

FIG. 8 depicts an enlarged view of the total ion chromatogram of the liquid (distillate) obtained in Example 10 (upper chart); and a mass spectrometric chart of the target compound (lower chart), as determined through gas chromatography-mass spectrometry (GC/MS).

FIG. 9 depicts an enlarged view of the total ion chromatogram of the liquid (distillate) obtained in Example 10 (upper chart); and a mass spectrometric chart of isomers (lower chart), as determined through gas chromatography-mass spectrometry (GC/MS).

FIG. 10 depicts a gas chromatographic chart of bicyclohexyl-3,3'-diene (including isomers) obtained in Example 10.

FIG. 11 depicts a total ion chromatogram of a solution obtained after the completion of dehydration in Example 2 (upper chart); and a mass spectrometric chart of 4-(3'-cyclohexenyl)cyclohexanol as a reaction intermediate (lower chart), as determined through gas chromatography-mass spectrometry (GC/MS).

BEST MODES FOR CARRYING OUT THE INVENTION

According to the present invention, a cyclic olefin compound having two or more cyclohexene rings per molecule is produced via intramolecular dehydration of an alicyclic alcohol having two or more hydroxylated cyclohexane rings per molecule (hereinafter also referred to as "substrate").

The alicyclic alcohol having two or more hydroxylated cyclohexane rings per molecule is not particularly limited, as long as being a compound having two or more hydroxylated cyclohexane rings per molecule, and examples thereof include compounds each composed of two hydroxycyclohexyl groups (2-hydroxycyclohexyl group, 3-hydroxycyclohexyl group, or 4-hydroxycyclohexyl group) bonded through a single bond or a bivalent group (e.g., a bivalent group Y mentioned below); compounds each composed of three hydroxycyclohexyl groups bonded through a trivalent group; compounds each composed of four hydroxycyclohexyl groups bonded through a tetravalent group; and polycyclic compounds each containing at least two hydroxylated cyclohexane rings.

Representative exemplary alicyclic alcohols each having two or more hydroxylated cyclohexane rings per molecule include alicyclic alcohols represented by Formula (1). In Formula (1), Y represents a bivalent group selected from single bond, oxygen atom, sulfur atom, —SO—, —SO$_2$—, and a halogenated or unhalogenated bivalent hydrocarbon group having a linear, branched, or cyclic skeleton and containing one to eighteen carbon atoms, or a bivalent group composed of two or more of these groups bonded with each other.

Exemplary halogen atoms include fluorine atom, chlorine atom, and bromine atom. Exemplary bivalent hydrocarbon groups each having a linear, branched, or cyclic skeleton and containing one to eighteen carbon atoms include linear or branched alkylene groups each containing one to eighteen carbon atoms, such as methylene, ethylene, methylmethylene, trimethylene, propylene, dimethylmethylene, tetramethylene, pentamethylene, hexamethylene, heptamethylene, octamethylene, and decamethylene groups; bivalent alicyclic hydrocarbon groups each containing three to eighteen carbon atoms, such as 1,2-cyclopentylene, 1,3-cyclopentylene, 1,2-cyclohexylene, 1,3-cyclohexylene, 1,4-cyclohexylene, cyclopentylidene, and cyclohexylidene groups; bivalent aromatic hydrocarbon groups each containing six to eighteen carbon atoms, such as 1,2-phenylene, 1,3-phenylene, and 1,4-phenylene groups; and alkylene groups each having a cyclic skeleton such as an aromatic hydrocarbon group or an alicyclic hydrocarbon group, such as phenylmethylene and cyclohexylmethylene groups. Exemplary halogenated bivalent hydrocarbon groups each having a linear, branched, or cyclic skeleton and containing one to eighteen carbon atoms include —C(Br)$_2$—, —C(CBr$_3$)$_2$—, and —C(CF$_3$)$_2$—.

Among them, preferred as Y are single bond, oxygen atom, sulfur atom, —SO—, —SO$_2$—, —CH$_2$—, —C(CH$_3$)$_2$—, —C(Br)$_2$—, —C(CBr$_3$)$_2$—, —C(CF$_3$)$_2$—, and a bivalent hydrocarbon group having a linear, branched, or cyclic skeleton and containing four to eighteen carbon atoms.

Specific exemplary alicyclic alcohols each having two or more hydroxylated cyclohexane rings per molecule include alicyclic alcohols each having two hydroxylated cyclohexane rings per molecule, such as hydrogenated biphenol, bis(cyclohexanol)methane, bis(dimethylcyclohexanol)methane, 1,2-bis(cyclohexanol)ethane, 1,3-bis(cyclohexanol)propane, 1,4-bis(cyclohexanol)butane, 1,5-bis(cyclohexanol)pentane, 1,6-bis(cyclohexanol)hexane, 2,2-bis(cyclohexanol)propane, bis(cyclohexanol)phenylmethane, 3,3-bis(cyclohexanol)pentane, 5,5-bis(cyclohexanol)heptane, 2,2-bis[4,4'-bis(cyclohexanol)cyclohexyl]propane, and dodecahydrofluorenediol; alicyclic alcohols each having three hydroxylated cyclohexane rings per molecule, such as α,α-bis(4-hydroxycyclohexyl)-4-(4-hydroxy-α,α-dimethylcyclohexyl)-ethylbenzene, tris(cyclohexanol)methane, tris(cyclohexanol)ethane, and 1,3,3-tris(cyclohexanol)butane; and alicyclic alcohols each having four hydroxylated cyclohexane rings per molecule, such as tetrakis(cyclohexanol)ethane. Among them, compounds each having two or more (e.g., two to four) 4-hydroxycyclohexyl groups, such as compounds represented by Formulae (1a), (1b), and (1c), are preferred as starting materials in the production method according to the present invention. Each of different alicyclic alcohols having two or more hydroxylated cyclohexane rings per molecule may be used alone or in combination.

The production method according to the present invention is characterized by including the step (i) of heating the alicyclic alcohol at a temperature of from 130° C. to 230° C. and a pressure greater than 20 Torr (2.67 kPa) in an organic solvent in the presence of a dehydration catalyst that is liquid or soluble in a liquid reaction mixture under the reaction conditions, to carry out dehydration of the alicyclic alcohol while distilling off by-product water; and the subsequent step (ii) of heating the resulting reaction mixture at a temperature of from 50° C. to 220° C. and a pressure of 200 Torr (26.7 kPa) or less to recover the cyclic olefin compound as a distillate.

Organic solvents for use in the step (i) are not particularly limited, as long as being solvents that are inert under the reaction conditions. Among such solvents, solvents that are liquid at 25° C. and have a boiling point of about 120° C. to 200° C. are preferred. Representative examples of preferred organic solvents include aromatic hydrocarbons such as xylenes, cumene, and pseudocumene; and aliphatic hydrocarbons such as dodecane and undecane. For separating and removing by-product water in a simple manner, an organic solvent that is azeotropic with water and is separable from water may also be used as the organic solvent. Ketones, esters, and other solvents that undergo reaction in the presence of an acid are undesirable herein, even they have a boiling point within the above-specified range. Alcohol solvents are also undesirable, because they may undergo dehydration.

The amount of organic solvents can be suitably set in consideration typically of operational ease (operability) and reaction rate, but is generally about 50 to 1000 parts by weight, and preferably about 90 to 900 parts by weight, to 100 parts by weight of the substrate alicyclic alcohol. The amount can also be selected within a range of from about 80 to 800 parts by weight, and preferably about 100 to 500 parts by weight, to 100 parts by weight of the substrate alicyclic alcohol.

Dehydration catalysts for use in the step (i) are not particularly limited, as long as having a dehydration activity and being liquid or soluble in a reaction mixture (fully soluble in the above-mentioned amount), but are preferably those having no or a minimized activity on the reaction solvent. Of dehydration catalysts that are liquid under the reaction conditions, preferred are those that are finely dispersed in the liquid reaction mixture. Exemplary generally used dehydration catalysts include acids including inorganic acids such as phosphoric acid and sulfuric acid, and sulfonic acids such as p-toluenesulfonic acid, benzenesulfonic acid, and naphthalenesulfonic acid; and salts of them, typified by fully neutralized salts and partially neutralized salts of the acids with organic bases. Each of different dehydration catalysts may be used alone or in combination.

When a neutralized salt of an acid with an organic base is used, the neutralized salt (fully neutralized salt or partially neutralized salt) may be isolated and purified from a reaction mixture obtained as a result of a reaction between the acid and the organic base, but the reaction mixture obtained as a result of a reaction between the acid and the organic base and containing a fully neutralized salt and/or a partially neutralized salt may also be used as intact as the neutralized salt. In the latter case, it is acceptable that the reaction mixture further contains a free acid. In the latter case, the ratio between the acid and the organic base may be such that the amount of the organic base is, for example, about 0.01 to 1 equivalent, preferably about 0.05 to 0.5 equivalent, and more preferably about 0.1 to 0.47 equivalent, per 1 equivalent of the acid. Typically, when a reaction mixture between sulfuric acid and an organic base is used, the ratio between sulfuric acid and the organic base may be such that the amount of the organic acid is preferably about 0.02 to 2 mole, more preferably about 0.1 to 1.0 mole, and particularly preferably about 0.2 to 0.95 mole, per 1 mole of sulfuric acid. When a neutralized salt of an acid with an organic base is used, the neutralized salt may be formed within the system by separately adding the acid and the organic base to the system.

The organic base can be any organic compound having basicity, and exemplary organic bases include amines such as 1,8-diazabicyclo[5.4.0]undecene-7 (DBU), 1,5-diazabicyclo[4.3.0]nonene-5 (DBN), piperidine, N-methylpiperidine, pyrrolidine, N-methylpyrrolidine, triethylamine, tributylamine, benzyldimethylamine, 4-dimethylaminopyridine, and N,N-dimethylaniline, of which tertiary amines are preferred; nitrogen-containing aromatic heterocyclic compounds such as pyridine, collidine, quinoline, and imidazole; guanidines; and hydrazines. Among them, preferred are tertiary amines such as 1,8-diazabicyclo[5.4.0]undecene-7 (DBU), 1,5-diazabicyclo[4.3.0]nonene-5 (DBN), triethylenediamine, and triethylamine (of which cyclic amines are more preferred); guanidines; and hydrazines, of which DBU, DBN, triethylenediamine, and triethylamine are especially preferred. Of such organic bases, preferred are those having a pKa of 11 or greater and those having a boiling point of 150° C. or higher.

It is possible to use sulfuric acid as intact as the dehydration catalyst, but industrial use of sulfuric acid as intact is difficult to some extent unless the concentration is strictly controlled, because the reaction period becomes excessively short in this case. Accordingly, sulfuric acid, if used, is desirably used as a salt with an organic base. In contrast, phosphoric acid and p-toluenesulfonic acid may be used as intact without converting into a salt, because these have a relatively low acidity.

Inorganic salts of sulfuric acid, such as potassium hydrogen sulfate, are not preferred as the dehydration catalyst. This is because such inorganic salts of sulfuric acid have very low solubility in a mixture of the reaction solvent and the substrate, should thereby be used in large amounts; but in this case, the residue of the reaction mixture after the completion of reaction, from which the target compound has been recovered, is a tarry material containing sulfate ions, and disposal or treatment of the residue, if the production increases, becomes significantly environmentally and economically disadvantageous. Additionally, ammonium salt of sulfuric acid (ammonium sulfate) is also not preferred as the dehydration catalyst, because this also has a low solubility in a mixture of the solvent and the substrate and should be used in a large amount.

Accordingly, preferred dehydration catalysts include sulfonic acids (e.g., p-toluenesulfonic acid), phosphoric acid, sulfuric acid, fully neutralized salts or partially neutralized salts of sulfonic acids (e.g., p-toluenesulfonic acid) with organic bases, fully neutralized salts or partially neutralized salts of phosphoric acid with organic bases, and fully neutralized salts or partially neutralized salts of sulfuric acid with organic bases. Among them, more preferred are sulfonic acids (of which p-toluenesulfonic acid is typically preferred), fully neutralized salts or partially neutralized salts of the sulfonic acids with organic bases, fully neutralized salts or partially neutralized salts of sulfuric acid with organic bases, and mixtures of these with sulfuric acid; of which further preferred are fully neutralized salts or partially neutralized salts (of which partially neutralized salts are more preferred) of sulfuric acid with organic bases, and mixtures of these with sulfuric acid.

The amount of dehydration catalysts is, of example, to 0.5 mole, preferably 0.001 to 0.47 mole (e.g., to 0.3 mol), and more preferably 0.005 to 0.45 mole (e.g., 0.005 to 0.2 mol), per 1 mole of the substrate alicyclic alcohol.

In combination with dehydration catalysts, an alkali metal salt of a carboxylic acid may be used as a reactivity modifier.

Exemplary alkali metal salts of carboxylic acids include alkali metal salts of carboxylic acids each containing about one to twenty carbon atoms, such as potassium formate, sodium formate, potassium acetate, sodium acetate, potassium propionate, sodium propionate, potassium octanoate, sodium octanoate, potassium stearate, and sodium stearate, of which alkali metal salts of saturated aliphatic carboxylic acids each containing about one to twenty carbon atoms are preferred. The amount of alkali metal salts of carboxylic acids is, for example, 0.00001 to 0.05 mole, preferably 0.00005 to 0.01 mole, and more preferably 0.0001 to 0.001 mole, per 1 mole of the substrate alicyclic alcohol.

Procedures, such as order and way, of adding an alicyclic alcohol as a starting material, an organic solvent, and a dehydration catalyst are not particularly limited in the step (i) (dehydration step). A reaction may be started after charging the whole quantities of the components such as the alicyclic alcohol and dehydration catalyst into the reaction system, or the reaction may be carried out while adding these components intermittently or continuously to the reaction system. More specifically but by way of example, in a possible process, a mixture of an alicyclic alcohol, a dehydration catalyst that is liquid or soluble in a liquid reaction mixture under the reaction conditions, and an organic solvent is prepared in advance and the mixture is heated at a temperature of from 130° C. to 230° C. and a pressure greater than 20 Torr (2.67 kPa) to carry out dehydration while distilling off by-product water. In another possible process, the dehydration is carried out by intermittently or continuously adding the alicyclic alcohol to the organic solvent at a pressure greater than 20 Torr (2.67 kPa) while distilling off by-product water, in which the organic solvent is heated at a temperature of from 130° C. to 230° C. and is coexistent with the dehydration catalyst that is liquid or soluble in a liquid reaction mixture under the reaction conditions.

The latter process is a process of carrying out dehydration by intermittently or continuously adding the alicyclic alcohol to the organic solvent in coexistence with the dehydration catalyst while distilling off by-product water (hereinafter briefly referred to as "alicyclic alcohol sequential addition process"). Employment of the latter process yields a great advantage of noticeably suppressing by-production of high-boiling impurities. Specifically, side reactions generally occur in a reaction system in addition to dehydration of an alicyclic alcohol. Exemplary side reactions include the aftermentioned isomerization; etherification; dimerization and polymerization (multimerization) via addition of hydroxyl groups typically of the starting material alicyclic alcohol to double bonds of dehydrated products (a target cyclic olefin compound, and a reaction intermediate having both a double bond and a hydroxyl group); and polymerization at the double bonds. Such side reactions yield by-product high-boiling compounds, in addition to the target compound and the reaction intermediate. Although being separable from the target cyclic olefin compound, the high-boiling compounds are difficult to be separated from each other and be purified, are hardly used effectively, and cause loss of the starting material. These lead to great economical and environmental (resource saving) disadvantages. However, employment of the alicyclic alcohol sequential addition process noticeably reduces formation of high-boiling compounds due to the side reactions, probably because this avoids accumulation of the alicyclic alcohol in the reaction system. The presence of these high-boiling compounds may be detected by determining the presence or absence of one or more peaks at retention times longer than that of the target cyclic olefin compound and a reaction intermediate (a reaction intermediate having both a double bond and a hydroxyl group) in gas chromatography and/or gas chromatography-mass spectrometry (GC/MS).

In the alicyclic alcohol sequential addition process, the period until the whole quantity of alicyclic alcohol is added to the reaction system may be suitably set in consideration typically of the operational ease and reaction rate, but is generally 10 minutes to 25 hours, preferably 15 minutes to 12 hours, and more preferably 20 minutes to 6 hours. If the alicyclic alcohol is added to the reaction system within a period shorter than 10 minutes, the added alicyclic alcohol may accumulate as unreacted in the reaction system to cause side reactions and resulting by-production of high-boiling compounds, thus being undesirable. In contrast, if the alicyclic alcohol is added to the reaction system over a period longer than 25 hours, it takes a long time to carry out the reaction, thus being energetically disadvantageous.

The step (i) and the step (ii) herein differ from each other in the pressure. A reaction mixture in the step (i) contains the unreacted alicyclic alcohol as a starting material; a reaction intermediate in which only one of two or more hydroxylated cyclohexane rings of the starting material alicyclic alcohol has undergone intramolecular dehydration into a cyclohexene ring (e.g., a compound represented by Formula (4)); the target cyclic olefin compound; by-product water; the dehydration catalyst; and the reaction solvent in coexistence. By-product water is distilled out (evaporated) in the step (i), but it is not desirable to distill out the reaction intermediate in this step for the following reasons. Specifically, (1) distilling out of the reaction intermediate causes reduction in the yield of the target compound, because the reaction intermediate can be converted into the target compound via further intramolecular dehydration; and (2) the reaction intermediate is generally a sublimable solid, and a sublimated reaction intermediate may deposit in a pathway for distillation of by-product water in a distillation column, if used, to block or clog the distillation pathway, and this invites increase in the inner pressure of the reactor, thus causing troubles such as a rupture or damage of the reactor and scattering of the reaction mixture. Accordingly, dehydration in the step (i) is carried out, while distilling off by-product water, at a pressure greater than 20 Torr (2.67 kPa) so as to avoid distillation of the reaction intermediate. The pressure is preferably greater than 20 Torr and equal to or less than normal pressure (atmospheric pressure) (greater than 2.67 kPa and equal to or less than 0.1 MPa), more preferably greater than 100 Torr and equal to or less than normal pressure (greater than 13.3 kPa and equal to or less than 0.1 MPa), and further preferably greater than 200 Torr and equal to or less than normal pressure (greater than 26.7 kPa and equal to or less than 0.1 MPa). From the viewpoint of operational ease, the pressure is typically preferably normal pressure (atmospheric pressure). The temperature (reaction temperature) in the step (i) is from 130° C. to 230° C. (e.g., 130° C. to 200° C.), preferably from 140° C. to 200° C. (e.g., 140° C. to 195° C.), and more preferably from 140° C. to 185° C. Dehydration at an excessively high temperature may cause side reactions such as isomerization, and dehydration at an excessively low temperature may cause an insufficient reaction rate. The reaction period is generally from about 1 to 10 hours, and preferably from about 2 to 6 hours. In the alicyclic alcohol sequential addition process, the reaction period from the time point upon the completion of the addition of the starting material is, for example, from about 0.5 to 10 hours, and preferably from about 1 to 6 hours.

On the other hand, the target cyclic olefin compound is recovered as a distillate from the reaction mixture from which by-product water has been distilled off. The reaction mixture obtained in the step (i) may be subjected to the step (ii)

without any treatment, but, if necessary, the reaction mixture may be subjected to a suitable treatment such as extraction, washing with water, and/or adjustment in acidity or alkalinity before subjected to the step (ii). When an organic solvent used in the reaction has a boiling point lower than that of a target cyclic olefin compound, the cyclic olefin compound is recovered as a distillate after distilling off the organic solvent.

In the step (ii), an operation is carried out at a pressure of 200 Torr (26.7 kPa) or less, because there is only little amount of the reaction intermediate in the step (ii), and even a low pressure may not cause problems such as blockage of the distillation pathway; and a high pressure may require a longer time period to recover the target compound as a distillate. The pressure in the step (ii) is preferably set lower than the pressure in the step (i). Typically, the different between the pressure in the step (i) and the pressure in the step (ii) [the former minus the latter] may be, for example, 100 Torr or more (13.3 kPa or more), preferably 200 Torr or more (26.7 kPa or more), and more preferably 500 Torr or more (66.7 kPa or more). The pressure in the step (ii) is preferably from about 3 to 200 Torr (from about 0.40 to 26.7 kPa), more preferably from about 3 to 100 Torr (from about 0.40 to 13.3 kPa), and further preferably from about 3 to 20 Torr (from about 0.40 to 2.67 kPa). The temperature in the step (ii) is from 50° C. to 220° C. (e.g., 100° C. to 220° C.), and preferably from 140° C. to 220° C. (e.g., 150° C. to 200° C.). The temperature in the step (ii) may also be selected within a range of from 120° C. to 180° C., and preferably within a range of from 130° C. and lower than 150° C. An excessively high temperature may cause occurrence of side reactions such as isomerization, and an excessively low temperature may cause an insufficient distillation rate.

A distillation apparatus, if attached typically to a reactor for the distillation typically of the target compound, is not particularly limited, as long as being a distillation apparatus that is commonly or generally used, such as a packed column or an Oldershaw distillation column, and having a satisfactory reflux ratio.

The target cyclic olefin compound recovered as a distillate in the step (ii) can be further purified according to necessity. When the distilled cyclic olefin compound contains a trace amount of water, the target cyclic olefin compound can be purified and separated by using the difference in specific gravity. In general, however, purification by distillation is preferred.

A compound represented by Formula (1), if used as a starting material alicyclic alcohol, gives a cyclic olefin compound represented by Formula (2) as a result of intramolecular dehydration.

According to the present invention, a starting material alicyclic alcohol is reacted under specific reaction conditions in an organic solvent in the presence of a dehydration catalyst that is liquid or soluble in a liquid reaction mixture under the reaction conditions while distilling off by-product water, and the resulting cyclic olefin compound is distilled out under specific conditions to recover as a distillate. The target reaction can thereby be conducted at a relatively low temperature within a relatively short period, side reactions such as isomerization can be suppressed, and problems or disadvantages, such as loss due to distillation out of a reaction intermediate and blockage due to sublimation of the reaction intermediate, are prevented. Accordingly, a high-purity cyclic olefin compound containing, if any, less impurities can be efficiently and simply obtained in a high yield. In contrast, known methods, such as the method described in JP-A No. 2000-169399, require a long reaction period, and this invites large amounts of undesirable by-products as a result of side reactions such as isomerization. Such by-product isomers have properties, such as the boiling point and solubility in an solvent, similar to those of the target compound, and once being formed, it is very difficult to separate them from the target compound. If a product cyclic olefin compound containing large amounts of the by-products is used as a curable resin typically after epoxidation, the by-products contained therein may cause an insufficient reactivity of the resin upon curing and may cause markedly impaired properties of the resulting cured article. In this connection, most of the isomers are difficult to be separated from the target compound when using a regular gas chromatographic system, and the yield and purity of the target compound may be indicated higher than their actual values. Accordingly, these isomers are preferably analyzed by gas chromatography using a capillary column which shows higher separability.

As is described above, the method according to the present invention can produce high-purity cyclic olefin compounds containing, if any, very small amounts of impurities such as isomers. The resulting cyclic olefin compounds may have a purity of, for example, 81.5% or more, preferably 82% or more, more preferably 84% or more, and particularly preferably 85% or more. By way of example, the method can produce a mixture of isomers of a cyclic olefin compound having two or more cyclohexene rings per molecule, in which the ratio of a major compound to isomers thereof (total of isomers differing from the major compound in the position of double bond) is from 81.5:18.5 to 99:1 in terms of an area ratio determined by gas chromatography (under some conditions, a cyclic olefin compound in which the ratio is 82:18 to 99:1, more preferably 84:16 to 99:1, and particularly preferably 85:15 to 99:1). By taking a representative example, an alicyclic alcohol represented by Formula (1) yields a cyclic olefin compound as a mixture of a cyclic olefin compound represented by Formula (2) with isomers as impurities, which differ from the cyclic olefin compound of Formula (2) in the position of double bond, in which the ratio of the former to the latter [the ratio of the cyclic olefin compound represented by Formula (2) to the total of isomers differing in the position of double bond] is 81.5:18.5 to 99:1 in terms of an area ratio determined by gas chromatography (under some conditions, a cyclic olefin compound in which the ratio is 82:18 to 99:1, more preferably 84:16 to 99:1, and particularly preferably 85:15 to 99:1, 85:15 to 99:1).

The resulting cyclic olefin compounds can be converted via epoxidation into epoxy compounds that are useful as curable resins.

EXAMPLES

The present invention will be illustrated in further detail with reference to several examples below. It should be noted, however, that these are illustrated only by way of example and are never construed to limit the scope of the present invention. Measurement conditions in gas chromatography and gas chromatography-mass spectrometry (GC/MS) are as follows.

(1) Gas Chromatography of Solution After Completion of Dehydration [Step (i)]

Measuring Device: GC-9A (Shimadzu Corporation)
Column: 5% SHINCARBON A/Thermon-3000
Column Size: 2.1 m in length and 2.6 mm in inner diameter
Detector: Flame ionization detector (FID)
Column Temperature: Holding at 60° C. for 2 minutes, heating to 270° C. at a rate of 10° C./min., and holding at 270° C.
Analysis Time: 38 min.
Injector Temperature: 250° C.
Detector Temperature: 260° C.

Injection Volume: 0.5 μL
Carrier Gas: Nitrogen
Carrier Gas Flow Rate: 40 mL/min.
Pneumatic Pressure: 0.6 kg/cm$^2$
Hydrogen Pressure: 0.6 kg/cm$^2$
Calculation of Concentration: Calculation based on a standard curve according to an internal standard method
Internal Standard: 1,4-Dioxane
Preparation of Analytical Sample: the Internal Standard is added in an amount of 50 percent by weight to a sample to be analyzed.

(2) Gas Chromatography-Mass Spectrometry (GC/MS) of Solution After Completion of Dehydration [Step (i)]
Measuring Device Gas chromatograph; HP 6890 (Hewlett-Packard Company), mass spectrometer; 5973 (Hewlett-Packard Company)
Column: HP-5MS (5%-diphenyl-95%-dimethylpolysiloxane)
Column Size: 30 m in length, 0.25 mm in inner diameter, and 0.25 μm in membrane thickness
Carrier Gas: Helium
Carrier Gas Flow Rate: 0.7 mL/min. (constant flow)
Split Ratio: 10:1
Column Temperature Holding at 60° C. for 2 minutes, heating to 300° C. at a rate of 10° C./min., and holding at 300° C. for 9 minutes
Analysis Time: 35 min.
Injector Temperature: 250° C.
Mass Selective Detector Transfer Line Temperature: 310° C.
Measurement Mode: Electron ionization/scanning
Ion Source Temperature: 230° C.
Quadrupole Temperature: 106° C.
Mass Spectrometry Range: m/z=25-400
Injection Volume: 1.0 μL
Preparation of Analytical Sample: Acetone (20 times by weight) is added to a sample to be analyzed.

(3) Gas Chromatography-1 of Cyclic Olefin Compound (Product) Distilled via Distillation [Step (ii)] (Examples 1 to 7, Comparative Examples 1 and Comparative Example 3)
Measuring Device: HP 6890 (Hewlett-Packard Company)
Column: HP-5, 5% phenylmethylsiloxane, 320 μm in diameter, 60 m in length
Detector: Flame ionization detector (FID)
Injector Temperature: 250° C.
Column Temperature Holding at 60° C. for 5 minutes and heating to 300° C. at a rate of 10° C./min.
Detector Temperature: 250° C.
Injection Volume: 1 μl, Split Ratio: 100:1
Carrier Gas: Nitrogen
Carrier Gas Flow Rate: 2.6 ml/min.
The ratio of a target compound to isomers was determined in the following manner. Specifically, gas chromatography was conducted under the above conditions, and the ratio of an area of a maximum peak appearing at a retention time of about 20.97 minutes (target compound) to an area of an immediately preceding peak appearing at a retention time of about 20.91 minutes (isomers) was determined and defined as the ratio in content of the target compound to the isomers.

(4) Gas Chromatography-2 of Cyclic Olefin Compound (Product) Distilled via Distillation [Step (ii)] (Examples 8 to 12)
Measuring Device: HP 6890 (Hewlett-Packard Company)
Column: HP-5 (5%-diphenyl-95%-dimethylpolysiloxane)
Column Size: 60 m in length, 0.32 mm in inner diameter, and 1.0 μm in membrane thickness
Carrier Gas: Nitrogen
Carrier Gas Flow Rate: 2.6 mL/min. (constant flow)
Split Ratio: 100:1
Column Temperature: Holding at 60° C. for 5 minutes, heating to 300° C. at a rate of 10° C./min., and holding at 300° C. for 1 minute
Analysis Time: 30 min.
Detector: Flame ionization detector (FID)
Injector Temperature: 250° C.
Detector Temperature: 250° C.
Hydrogen Flow Rate: 40.0 mL/min.
Air Flow Rate: 450.0 mL/min.
Makeup Gas: Nitrogen
Makeup Gas Flow Rate: 5.0 mL/min.
Injection Volume: 1.0 μL
Preparation of Analytical Sample: 2-Propanol (30 times by weight) is added to a sample to be analyzed
The ratio of a target compound to isomers was determined in the following manner. Specifically, gas chromatography was conducted under the above conditions, and the ratio of an area of a maximum peak appearing at a retention time of about 21.13 minutes (target compound) to an area of an immediately preceding peak appearing at a retention time of about 21.06 minutes (isomers) was determined and defined as the ratio in content of the target compound to the isomers.

(5) Gas Chromatography-Mass Spectrometry (GC/MS)-1 of Cyclic Olefin Compound (Product) Distilled via Distillation [Step (ii)] (Detection of Isomer; Comparative Example 3)
Column: DB-WAX 30 m
Oven Temperature: 200° C.
Injector Temperature: 230° C.
Detector Temperature: 230° C.
Carrier Gas: Helium
Carrier Gas Flow Rate: 1 ml/min.
Preparation of Analytical Sample: A Sample to be Analyzed is diluted with acetone to give a 1 percent by weight solution and subjected to analysis.

(6) Gas Chromatography-Mass Spectrometry (GC/MS)-2 of Cyclic Olefin Compound (Product) Distilled via Distillation [Step (ii)] (Detection of Isomers; Example 10)
Measuring Device: Gas chromatograph; HP 6890 (Hewlett-Packard Company), mass spectrometer; 5973 (Hewlett-Packard Company)
Column: HP-5MS (5%-diphenyl-95%-dimethylpolysiloxane)
Column Size: 30 m in length, 0.25 mm in inner diameter, and 0.25 μm in membrane thickness
Carrier Gas: Helium
Carrier Gas Flow Rate: 0.7 mL/min. (constant flow)
Split Ratio: 100:1
Column Temperature: Holding at 100° C. for 2 minutes, heating to 300° C. at a rate of 5° C./min., and holding at 300° C. for 18 minutes
Analysis Time: 60 min.
Injector Temperature: 250° C.
Mass Selective Detector Transfer Line Temperature: 280° C.
Measurement Mode: Electron ionization/scanning
Ion Source Temperature: 230° C.
Quadrupole Temperature: 106° C.
Mass Spectrometry Range: m/z=25-400
Injection Volume: 1.0 μL
Preparation of Analytical Sample: Acetone (40 times by weight) is added to a sample to be analyzed.

Example 1

In a 3-liter flask equipped with a stirrer, a thermometer, and a distillation line provided with a water outlet and kept at a constant temperature, were placed 840 g (4.24 mol) of a hydrogenated biphenol represented by following Formula (1a):

[Chemical Formula 17]

(1a)

140 g (0.81 mol) of p-toluenesulfonic acid, and 1800 g of cumene, and the flask was heated. Formation of water from around the time when the inner temperature exceeded 110° C. The heating was further continued to raise the temperature to the boiling point of cumene (inner temperature: 162° C. to 172° C.), and dehydration was conducted under normal pressure. By-product water was distilled off and discharged from the system via the water outlet. In this process, p-toluenesulfonic acid was fully dissolved in the liquid reaction mixture under the reaction conditions.

After a lapse of four hours, a substantially theoretical amount of water (150 g) was distilled, whereby the reaction was completed. Using a 10-tray Oldershaw distillation column, cumene was distilled off from the resulting reaction mixture, and the residue was further subjected to distillation at an inner temperature of 138° C. to 142° C. and an inner pressure of 10 Torr (1.33 kPa), to thereby yield 474.2 g of bicyclohexyl-3,3'-diene represented by following Formula (3a):

[Chemical Formula 18]

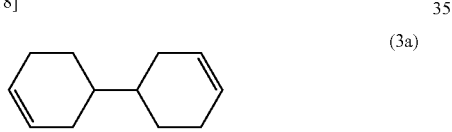

(3a)

The ratio in content of the target compound to isomers was 88:12 as determined by gas chromatography.

Example 2

A dehydration catalyst was prepared by blending 70 g (0.68 mol) of 95 percent by weight sulfuric acid and 55 g (0.36 mol) of 1,8-diazabicyclo[5.4.0]undecene-7 (DBU). In a 3-liter flask equipped with a stirrer, a thermometer, and a distillation line provided with a water outlet and kept at a constant temperature, were placed 1000 g (5.05 mol) of the hydrogenated biphenol, 125 g (0.68 mol in terms of sulfuric acid) of the above-prepared dehydration catalyst, and 1500 g of pseudocumene, and the flask was heated. Formation of water was detected from around the time when the inner temperature exceeded 115° C. The heating was further continued until the temperature reached the boiling point of pseudocumene (until being in a boiling state) (inner temperature: 162° C. to 170° C.), and dehydration was conducted under normal pressure. By-product water was distilled off and discharged from the system via the water outlet. Under the reaction conditions, the dehydration catalyst was liquid and finely dispersed in the liquid reaction mixture. After a lapse of three hours, a substantially theoretical amount of water (180 g) was distilled, whereby the reaction was completed.

The resulting reaction mixture was cooled to room temperature to separate into a tarry precipitate and a solution portion. The solution portion had a weight of 2320 g and a concentration of target bicyclohexyl-3,3'-diene of 32% as determined through gas chromatography, to find that the total weight of the target compound (bicyclohexyl-3,3'-diene) and isomers thereof was 738 g (4.55 mol, in a yield of 90%). In gas chromatography-mass spectrometry (GC/MS) were detected a reaction intermediate 4-(3'-cyclohexenyl)cyclohexanol represented by following Formula (4):

[Chemical Formula 19]

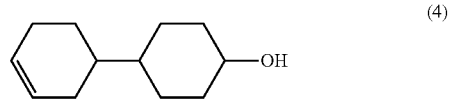

(4)

at a retention time of 14.3 minutes, followed by a variety of peaks (see FIG. 11). In FIG. 11, the upper chart depicts a total ion chromatogram, and the lower chart depicts a mass spectrometric chart of the reaction intermediate detected at a retention time of 14.3 minutes.

Using a 10-tray Oldershaw distillation column, pseudocumene was distilled off from the resulting reaction mixture, and the residue was further subjected to distillation at an inner temperature of 137° C. to 140° C. and an inner pressure of 10 Torr (1.33 kPa), to thereby yield 731 g (4.50 mol) of bicyclohexyl-3,3'-diene including isomers thereof. The yield on the basis of the hydrogenated biphenol used in dehydration was 89%. The ratio in content of the target compound to isomers was 91:9 as determined by gas chromatography (see FIG. 1).

Example 3

A dehydration catalyst was prepared by blending 94.5 g (0.916 mol) of 95 percent by weight sulfuric acid and 126.3 g (0.831 mol) of 1,8-diazabicyclo[5.4.0]undecene-7 (DBU).

In a 5-liter flask equipped with a stirrer, a 20-tray Oldershaw distillation column, and a thermometer were placed 2000 g (10.1 mol) of the hydrogenated biphenol, 220.8 g (0.916 mol in terms of sulfuric acid) of the above-prepared dehydration catalyst, and 2400 g of pseudocumene, and the flask was heated. Formation of water was detected from around the time when the inner temperature exceeded 115° C. The heating was further continued, and the reaction was continued to raise the temperature to the boiling point of pseudocumene (until being in a boiling state) (inner temperature: 165° C. to 171° C.) while by-product water was distilled off as an overhead from the distillation column, and thus dehydration was conducted under normal pressure. Under the reaction conditions, the dehydration catalyst was liquid and finely dispersed in the liquid reaction mixture. After a lapse of four and a half hours, 96% of the theoretical amount of water (384 g) was distilled, whereby the reaction was completed.

The resulting reaction mixture was cooled to room temperature to separate into a tarry precipitate and a solution portion. The solution portion had a weight of 4016 g and a concentration of target bicyclohexyl-3,3'-diene of 37.5% as determined by gas chromatography, to find that the total weight of the target compound (bicyclohexyl-3,3'-diene) and isomers thereof in the reaction mixture was 1506 g (9.28 mol, in a yield of 92%). In gas chromatography-mass spectrometry (GC/MS) were detected a reaction intermediate 4-(3'-cyclohexenyl)cyclohexanol at a retention time of 14.3 minutes, followed by a variety of peaks.

After the completion of reaction, pseudocumene was distilled off under reduced pressure, and the system was further evacuated to a pressure of 10 Torr (1.33 kPa) to carry out distillation at an inner temperature of 138° C. to 141° C., to yield 1491.2 g (9.19 mol) of bicyclohexyl-3,3'-diene including isomers thereof. The yield on the basis of the hydrogenated biphenol used in dehydration was 91%. The ratio in content of the target compound to isomers was 90:10 as determined by gas chromatography.

Example 4

In a 3-liter flask equipped with a stirrer, a thermometer, and a distillation line provided with a water outlet and kept at a constant temperature, were placed 840 g (4.24 mol) of the hydrogenated biphenol, 170 g (0.99 mol) of p-toluenesulfonic acid, and 2350 g of undecane, and the flask was heated. Formation of water was detected from around the time when the inner temperature exceeded 110° C. The heating was further continued until the temperature reached the boiling point of undecane (inner temperature: 185° C. to 191° C.), and dehydration was conducted under normal pressure. By-product water was distilled off and discharged from the system via the water outlet. In this process, p-toluenesulfonic acid was fully dissolved in the liquid reaction mixture under the reaction conditions.

After a lapse of four hours, a substantially theoretical amount of water (150 g) was distilled, whereby the reaction was completed. Using a 10-tray Oldershaw distillation column, undecane was distilled off from the resulting reaction mixture, and the residue was further subjected to distillation at an inner temperature of 137° C. to 141° C. and an inner pressure of 10 Torr (1.33 kPa), to thereby yield 474.2 g of bicyclohexyl-3,3'-diene. The ratio in content of the target compound to isomers was 88:12 as determined by gas chromatography.

Example 5

In a 3-liter flask equipped with a stirrer, a thermometer, and a distillation line provided with a water outlet and kept at a constant temperature, were placed 840 g (4.24 mol) of the hydrogenated biphenol, 170 g (1.73 mol) of phosphoric acid, and 2350 g of undecane, and the flask was heated. Formation of water was detected from around the time when the inner temperature exceeded 110° C. The heating was further continued until the temperature reached the boiling point of undecane (inner temperature: 189° C. to 194° C.), and dehydration was conducted under normal pressure. By-product water was distilled off and discharged from the system via the water outlet. In this process, p-toluenesulfonic acid was fully dissolved in the liquid reaction mixture under the reaction conditions.

After a lapse of five and a half hours, a substantially theoretical amount of water (150 g) was distilled, whereby the reaction was completed. Using a 10-tray Oldershaw distillation column, undecane was distilled off from the resulting reaction mixture, and the residue was further subjected to distillation at an inner temperature of 138° C. to 141° C. and an inner pressure of 10 Torr (1.33 kPa) and thereby yielded 474.2 g of bicyclohexyl-3,3'-diene. The ratio in content of the target compound to isomers was 87:13 as determined by gas chromatography.

Example 6

A dehydration catalyst was prepared by blending 101 g (1.00 mol) of triethylamine and 103 g (1.05 mol) of sulfuric acid.

In a 3-liter flask equipped with a stirrer, a thermometer, and a distillation line provided with a water outlet and kept at a constant temperature, were placed 840 g (4.24 mol) of the hydrogenated biphenol, 2350 g of undecane, and 159 g of the above-prepared dehydration catalyst, and the flask was heated. Formation of water was detected from around the time when the inner temperature exceeded 110° C. The heating was further continued until the temperature reached the boiling point of undecane (inner temperature: 185° C. to 191° C.), and dehydration was conducted under normal pressure. By-product water was distilled off and discharged from the system via the water outlet.

After a lapse of five and a half hours, a substantially theoretical amount of water (151 g) was distilled, whereby the reaction was completed. Using a 10-tray Oldershaw distillation column, undecane was distilled off from the resulting reaction mixture, and the residue was further subjected to distillation at an inner temperature of 136° C. to 141° C. and an inner pressure of 10 Torr (1.33 kPa), to thereby yield 473.9 g of bicyclohexyl-3,3'-diene. The ratio in content of the target compound to isomers was 92:8 as determined by gas chromatography.

Example 7

A dehydration catalyst was prepared by blending 145.4 g (1.44 mol) of triethylamine and 118 g (1.20 mol) of sulfuric acid.

In a 3-liter flask equipped with a stirrer, a thermometer, and a distillation line provided with a water outlet and kept at a constant temperature, were placed 840 g (4.24 mol) of the hydrogenated biphenol, 0.16 g (0.0019 mol) of sodium acetate, 2350 g of pseudocumene, and 157 g of the above-prepared dehydration catalyst, and the flask was heated. Formation of water was detected from around the time when the inner temperature exceeded 110° C. The heating was further continued until the temperature reached the boiling point of pseudocumene (inner temperature: 168° C. to 171° C.), and dehydration was conducted under normal pressure. By-product water was distilled off and discharged from the system via the water outlet.

After a lapse of five hours, a substantially theoretical amount of water (150 g) was distilled, whereby the reaction was completed. Using a 10-tray Oldershaw distillation column, pseudocumene was distilled off from the resulting reaction mixture, and the residue was further subjected to distillation at an inner temperature of 138° C. to 143° C. and an inner pressure of 10 Torr (1.33 kPa) and thereby yielded 479.3 g of bicyclohexyl-3,3'-diene. The ratio in content of the target compound to isomers was 90:10 as determined by gas chromatography.

Example 8

A dehydration catalyst was prepared by blending 62 g (0.61 mol) of 95 percent by weight sulfuric acid and 78 g (0.51 mol) of 1,8-diazabicyclo[5.4.0]undec-7-ene (DBU).

In a 3-liter flask equipped with a stirrer, a thermometer, and a distillation line provided with a water outlet and kept at a constant temperature, were placed 140 g (0.61 mol in terms of sulfuric acid) of the above-prepared dehydration catalyst, 300 g (1.5 mol) of the hydrogenated biphenol, and 2400 g of pseudocumene, and the flask was heated. The temperature was raised to a boiling state (inner temperature: 165° C. to 172° C.), and dehydration was conducted under normal pressure for three hours. By-product water was distilled off and discharged from the system via the water outlet. Under the reaction conditions, the dehydration catalyst was liquid and finely dispersed in the liquid reaction mixture.

The resulting reaction mixture was cooled to room temperature to separate into a tarry precipitate and a solution portion. The solution portion had a weight of 2658 g and a concentration of the target bicyclohexyl-3,3'-diene of 7.8% as determined through gas chromatography, to find that the total weight of the target compound (bicyclohexyl-3,3'-diene) and isomers thereof in the reaction mixture was 206 g (1.27 mol, in a yield of 84%). In gas chromatography-mass spectrometry (GC/MS) were detected a reaction intermediate 4-(3'-cyclohexenyl)cyclohexanol at a retention time of 14.3 minutes, followed by a variety of peaks.

Next, using a 10-tray Oldershaw distillation column, pseudocumene was distilled off from the resulting reaction mixture, and the residue was further subjected to distillation at an inner temperature of 137° C. to 141° C. and an inner pressure of 10 Torr (1.33 kPa), to thereby yield 204 g (1.26 mol) of bicyclohexyl-3,3'-diene including isomers thereof. The yield on the basis of the hydrogenated biphenol used in dehydration was 83%. The ratio in content of the target compound (bicyclohexyl-3,3'-diene) to isomers thereof was 91:9 as determined by gas chromatography.

Example 9

A dehydration catalyst was prepared by blending 103 g (1.0 mol) of 95 percent by weight sulfuric acid and 101 g (1.0 mol) of triethylamine.

In a 3-liter flask equipped with a stirrer, a thermometer, and a distillation line provided with a water outlet and kept at a constant temperature, were placed 159 g (1.0 mol in terms of sulfuric acid) of the above-prepared dehydration catalyst, 840 g (4.2 mol) of the hydrogenated biphenol, and 2400 g of pseudocumene, and the flask was heated. The temperature was raised to a boiling state (inner temperature: 165° C. to 172° C.), and dehydration was conducted under normal pressure for three hours. By-product water was distilled off and discharged from the system via the water outlet. Under the reaction conditions, the dehydration catalyst was liquid and finely dispersed in the liquid reaction mixture.

The resulting reaction mixture was cooled to room temperature to separate into a tarry precipitate and a solution portion. The solution portion had a weight of 2658 g and a concentration of the target bicyclohexyl-3,3'-diene of 7.8% as determined by gas chromatography, to find that the total weight of the target compound (bicyclohexyl-3,3'-diene) and isomers thereof in the reaction mixture was 479 g (2.95 mol, in a yield of 84%). In gas chromatography-mass spectrometry (GC/MS) were detected a reaction intermediate 4-(3'-cyclohexenyl)cyclohexanol at a retention time of 14.4 minutes, followed by a variety of peaks.

Next, using a 10-tray Oldershaw distillation column, pseudocumene was distilled off from the resulting reaction mixture, and the residue was further subjected to distillation at an inner temperature of 137° C. to 141° C. and an inner pressure of 10 Torr (1.33 kPa), to thereby yield 474 g (2.92 mol) of bicyclohexyl-3,3'-diene including isomers thereof. The yield on the basis of the hydrogenated biphenol used in dehydration was 83%. The ratio in content of the target compound (bicyclohexyl-3,3'-diene) to isomers thereof was 91:9 as determined by gas chromatography.

Comparative Example 1

In a 5-liter flask equipped with a stirrer, a 20-tray Oldershaw distillation column, and a thermometer were placed 1000 g (5.05 mol) of the hydrogenated biphenol, 40 g (0.265 mol) of ammonium hydrogen sulfate, and 2800 g of cumene, and the flask was heated. Formation of water was detected from around the time when the inner temperature exceeded 115° C. The heating was further continued, and the reaction was continued to raise the temperature to the boiling point of cumene (inner temperature: 165° C. to 170° C.), and dehydration was conducted under normal pressure while by-product water was distilled off as an overhead from the distillation column. In this process, ammonium hydrogen sulfate was solid and most thereof was not dissolved in the liquid reaction mixture under the reaction conditions.

After a lapse of six and a half hours, 94% of the theoretical amount of water (170.9 g) was distilled, whereby the reaction was completed. After the completion of reaction, cumene was distilled off under reduced pressure, and the system was further evacuated to a pressure of 10 Torr (1.33 kPa), followed by distillation at an inner temperature of 137° C. to 141° C., to yield 590 g of bicyclohexyl-3,3'-diene. The ratio in content of the target compound to isomers was 81:19 as determined by gas chromatography.

Comparative Example 2

In a 3-liter flask equipped with a stirrer, a thermometer, and a distillation line provided with a water outlet and kept at a constant temperature, were placed 640 g (3.23 mol) of the hydrogenated biphenol, 375 g (2.75 mol) of potassium hydrogen sulfate, and 1485 g of cumene, and the flask was heated. Formation of water was detected from around the time when the inner temperature exceeded 125° C. The heating was further continued until the temperature reached the boiling point of cumene (inner temperature: 166° C. to 170° C.), and dehydration was conducted under normal pressure. By-product water was distilled off and discharged from the system via the water outlet. In this process, potassium hydrogen sulfate was solid and most thereof was not dissolved in the liquid reaction mixture under the reaction conditions.

After a lapse of six and a half hours, only about one-third of the theoretical amount of water (35.9 g) was distilled, and the reaction was discontinued.

Comparative Example 3

In a 10-liter four-necked flask equipped with a stirrer, a 20-tray distillation column, and a thermometer were placed 6 kg of the hydrogenated biphenol and 620 g of potassium hydrogen sulfate. Next, the flask was heated to 180° C. to melt the hydrogenated biphenol, followed by stirring. The reaction was continued while by-product water was distilled off as an overhead from the distillation column. After a lapse of three hours, the reaction system was evacuated to a pressure of 10 Torr (1.33 kPa), and water and bicyclohexyl-3,3'-diene were continuously distilled out of the system from the uppermost tray of the distillation column. The water and bicyclohexyl-3,3'-diene distilled out of the system were separated into two layers in a decanter, and the upper layer alone was recovered. Thereafter, the reaction temperature was raised to 220° C. over four hours, and the reaction was completed at the time when distillation of water and bicyclohexyl-3,3'-diene was ceased. A crude distillate of bicyclohexyl-3,3'-diene was obtained in a yield of 4507 g.

In a 5-liter four-necked flask equipped with a stirrer, a 20-tray distillation column, and a thermometer was placed 4500 g of the crude distillate of bicyclohexyl-3,3'-diene, the temperature of the flask was raised to 180° C. on an oil bath. The reaction system was then evaluated to a pressure of 10

Torr (1.33 kPa) to distil off water, thereafter bicyclohexyl-3,3'-diene was purified by distillation at a reflux ratio of 1 over five hours, while keeping the temperature of the uppermost tray of the distillation column at 145° C., to thereby yield a colorless transparent liquid in a yield of 4353 g. The liquid was found to have a ratio in content of bicyclohexyl-3,3'-diene to isomers of 80:20 as determined by gas chromatography.

Additionally, gas chromatography-mass spectrometry (GC/MS) of the colorless transparent liquid was conducted under the above conditions.

Charts obtained in the gas chromatography-mass spectrometry (GC/MS) are shown in FIGS. 2, 3 and 4. FIG. 2 depicts a total ion chromatogram; FIG. 3 depicts a total ion chromatogram (upper chart) and a mass spectrometric chart of the target compound (bicyclohexyl-3,3'-diene) (lower chart); and FIG. 4 depicts a total ion chromatogram (upper chart) and a mass spectrometric chart of isomers (bicyclohexyl-2,2'-diene and bicyclohexyl-2,3'-diene) (lower chart). In these figures, symbol "A" represents a peak derived from the target compound, and symbol "B" represents a peak derived from the isomers. The target compound and the isomers have the same molecular weight and thereby have similar mass patterns, but they differ in the intensities of the respective fragment peaks.

Example 10

A dehydration catalyst was prepared by blending 62 g (0.61 mol) of 95 percent by weight sulfuric acid and 78 g (0.51 mol) of 1,8-diazabicyclo[5.4.0]-undec-7-ene.

In a 3-liter flask equipped with a stirrer, a thermometer, and a distillation line provided with a water outlet and kept at a constant temperature, were placed 140 g (0.61 mol in terms of sulfuric acid) of the above-prepared dehydration catalyst and 1200 g of pseudocumene, and the flask was heated. From the time when the liquid in the flask boiled and the inner temperature reached 175° C., 280 g (1.41 mol) of the hydrogenated biphenol represented by Formula (1a) was added intermittently over 45 minutes, and dehydration was then conducted while the boiling state was maintained (inner temperature: 175° C. to 178° C.) under normal pressure for three hours. By-product water was distilled off and discharged from the system via the water outlet. Under the reaction conditions, the dehydration catalyst was liquid and finely dispersed in the liquid reaction mixture.

The resulting reaction mixture was cooled to room temperature to separate into a tarry precipitate and a solution portion. The solution portion had a weight of 2589 g and had a concentration of the target compound bicyclohexyl-3,3'-diene represented by Formula (3a) of 8.6% as determined by gas chromatography (see FIG. 5), to find that the total weight of the target compound (bicyclohexyl-3,3'-diene) and isomers thereof in the reaction mixture was 224 g (1.38 mol, in a yield of 98%). In gas chromatography-mass spectrometry (GC/MS) was detected a reaction intermediate 4-(3'-cyclohexenyl)cyclohexanol represented by Formula (4) at a retention time of 14.4 minutes, but no subsequent component was detected (see FIG. 6).

Next, using a 10-tray Oldershaw distillation column, pseudocumene was distilled off from the resulting reaction mixture, and the residue was further subjected to distillation at an overhead temperature of 107° C. and a pressure of 10 Torr (1.33 kPa), to thereby yield 221 g (1.36 mol) of bicyclohexyl-3,3'-diene including isomers, as a distillate, in which the presence of isomers in the distillate was verified by gas chromatography-mass spectrometry (GC/MS) (see FIGS. 7 to 9). The yield on the basis of the hydrogenated biphenol used in dehydration was 97%. The ratio in content of the target compound (bicyclohexyl-3,3'-diene) to isomers thereof was 90:10 as determined by gas chromatography (see FIG. 10).

Of the charts obtained in the gas chromatography-mass spectrometry (GC/MS), FIG. 7 depicts a total ion chromatogram; FIG. 8 depicts an enlarged view of the total ion chromatogram (upper chart) and a mass spectrometric chart of the target compound (bicyclohexyl-3,3'-diene) (lower chart); and FIG. 9 depicts an enlarged view of the total ion chromatogram (upper chart) and a mass spectrometric chart of isomers (lower chart). In the total ion chromatogram, a component at a longer retention time is the target compound, and a component at a shorter retention time is isomers. The target compound and the isomers have the same molecular weight and thereby have similar mass patterns, but they differ in the intensities of the respective fragment peaks.

Example 11

A dehydration catalyst was prepared by blending 70 g (0.68 mol) of 95 percent by weight sulfuric acid and 87 g (0.57 mol) of 1,8-diazabicyclo[5.4.0]-undec-7-ene.

In a 3-liter flask equipped with a stirrer, a thermometer, and a distillation line provided with a water outlet and kept at a constant temperature, were placed 157 g (0.68 mol in terms of sulfuric acid) of the above-prepared dehydration catalyst and 1908 g of pseudocumene, and the flask was heated. From the time when the liquid in the flask boiled and the inner temperature reached 174° C., 504 g (2.5 mol) of hydrogenated biphenol was intermittently added over three hours, and dehydration was conducted while the boiling state was maintained (inner temperature: 174° C. to 178° C.) under normal pressure for five hours. By-product water was distilled off and discharged from the system via the water outlet. Under the reaction conditions, the dehydration catalyst was liquid and finely dispersed in the liquid reaction mixture.

The resulting reaction mixture was cooled to room temperature to separate into a tarry precipitate and a solution portion. The solution portion had a weight of 2321 g and a concentration of the target bicyclohexyl-3,3'-diene of 17.1% as determined by gas chromatography, to find that the total weight of the target compound (bicyclohexyl-3,3'-diene) and isomers thereof in the reaction mixture was 397 g (2.45 mol, in a yield of 96%). In gas chromatography-mass spectrometry (GC/MS) was detected a reaction intermediate 4-(3'-cyclohexenyl)cyclohexanol at a retention time of 14.4 minutes, but no subsequent component was detected.

Next, using a 10-tray Oldershaw distillation column, pseudocumene was distilled off from the resulting reaction mixture, and the residue was further subjected to distillation at an overhead temperature of 107° C. and a pressure of 10 Torr (1.33 kPa), to thereby yield 393 g (2.42 mol) of bicyclohexyl-3,3'-diene including isomers. The yield on the basis of hydrogenated biphenol used in dehydration was 95%. The ratio in content of the target compound (bicyclohexyl-3,3'-diene) to isomers thereof was 90:10 as determined by gas chromatography.

Example 12

A dehydration catalyst was prepared by blending 77 g (0.74 mol) of 95 percent by weight sulfuric acid and 63 g (0.63 mol) of triethylamine.

In a 3-liter flask equipped with a stirrer, a thermometer, and a distillation line provided with a water outlet and kept at a constant temperature, were placed 140 g (0.74 mol in terms of sulfuric acid) of the above-prepared dehydration catalyst and 2418 g of pseudocumene, and the flask was heated. From the time when the liquid in the flask boiled and the inner temperature reached 175° C., 359 g (1.8 mol) of hydrogenated biphenol was intermittently added over 50 minutes, and dehydration was conducted while the boiling state was maintained (inner temperature: 175° C. to 178° C.) under normal pressure for three hours. By-product water was distilled off and discharged from the system via the water outlet. Under the reaction conditions, the dehydration catalyst was liquid and finely dispersed in the liquid reaction mixture.

The resulting reaction mixture was cooled to room temperature to separate into a tarry precipitate and a solution portion. The solution portion had a weight of 2719 g and a concentration of the target bicyclohexyl-3,3'-diene of 9.2% as determined by gas chromatography, to find that the total weight of the target compound (bicyclohexyl-3,3'-diene) and isomers thereof in the reaction mixture was 250 g (1.54 mol, in a yield of 85%). In gas chromatography-mass spectrometry (GC/MS) was detected a reaction intermediate 4-(3'-cyclohexenyl)cyclohexanol at a retention time of 14.4 minutes, but no subsequent component was detected.

Next, using a 10-tray Oldershaw distillation column, pseudocumene was distilled off, and the resulting reaction mixture was then further subjected to distillation at an overhead temperature of 107° C. and a pressure of 10 Torr (1.33 kPa), to thereby yield 247 g (1.52 mol) of bicyclohexyl-3,3'-diene including isomers. The yield on the basis of hydrogenated biphenol used in dehydration was 84%. The ratio in content of the target compound (bicyclohexyl-3,3'-diene) to isomers thereof was 86:14 as determined by gas chromatography.

Comparative Example 4

In a 3-liter flask equipped with a stirrer, a thermometer, and a distillation line provided with a water outlet and kept at a constant temperature, were placed 126 g (0.93 mol) of sodium hydrogen sulfate and 2160 g of pseudocumene, and the flask was heated. From the time when the liquid in the flask boiled and the inner temperature reached 176° C., 280 g (1.41 mol) of the hydrogenated biphenol was added intermittently over 50 minutes, and dehydration was then conducted while the boiling state was maintained (inner temperature: 176° C. to 178° C.) under normal pressure for two hours, but there was not observed distillation of water, whereby the reaction was finished.

The resulting liquid reaction mixture was cooled to room temperature to find that unreacted hydrogenated biphenol deposited. Thus, filtration was conducted to recover 1969 g of a filtrate. The filtrate had a concentration of the target compound bicyclohexyl-3,3'-diene of 0.3% as determined through gas chromatography, to find that the total weight of the target compound (bicyclohexyl-3,3'-diene) and isomers thereof in the reaction mixture was 5.7 g (0.03 mol, in a yield of 2%). Accordingly, the filtrate was not subjected to gas chromatography-mass spectrometry (GC/MS) and further purification through distillation.

Industrial Applicability

The method according to the present invention simply and industrially efficiently produces high-purity cyclic olefin compounds in high yields, which cyclic olefin compounds contain less impurities such as isomers.

The invention claimed is:

1. A method for producing a cyclic olefin compound having two or more cyclohexene rings per molecule via intramolecular dehydration of an alicyclic alcohol having two or more hydroxylated cyclohexane rings per molecule, the method comprising the step (i) of heating the alicyclic alcohol at a temperature of from 130° C. to 230° C. and a pressure greater than 20 Torr (2.67 kPa) in an organic solvent in the presence of a dehydration catalyst to carry out dehydration of the alicyclic alcohol while distilling off by-product water, the dehydration catalyst being liquid or soluble in a liquid reaction mixture under the reaction conditions; and the subsequent step (ii) of heating the resulting reaction mixture at a temperature of from 50° C. to 220° C. and a pressure of 200 Torr (26.7 kPa) or less to recover the cyclic olefin compound as a distillate, wherein the dehydration in the step (i) is carried out by intermittently or continuously adding the alicyclic alcohol to the organic solvent at a pressure greater than 20 Torr (2.67 kPa) while distilling off by-product water, in which the organic solvent is heated at a temperature of from 130° C. to 230° C. and is coexistent with the dehydration catalyst that is liquid or soluble in a liquid reaction mixture under the reaction conditions, and wherein the dehydration catalyst that is liquid or soluble in a liquid reaction mixture under the reaction conditions is a fully neutralized salt or partially neutralized salt of a sulfonic acid with an organic base, a fully neutralized salt or partially neutralized salt of sulfuric acid with an organic base, or mixtures thereof with sulfuric acid.

2. The method for producing a cyclic olefin compound, according to claim 1, wherein the method comprises carrying out intramolecular dehydration of an alicyclic alcohol represented by following Formula (1):

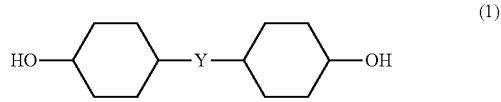

wherein Y represents a bivalent group selected from the group consisting of single bond, oxygen atom, sulfur atom, —SO—, —SO₂—, and a halogenated or unhalogenated bivalent hydrocarbon group having a linear, branched, or cyclic skeleton and containing one to eighteen carbon atoms, or a bivalent group composed of two or more of these groups bonded with each other, to yield a cyclic olefin compound represented by following Formula (2):

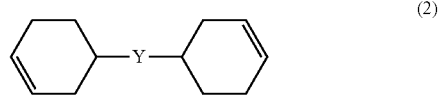

wherein Y is as defined above.

3. The method for producing a cyclic olefin compound, according to claim 1, wherein the organic solvent is at least one solvent selected from the group consisting of aromatic hydrocarbons and aliphatic hydrocarbons.

4. The method for producing a cyclic olefin compound, according to claim 1, wherein the dehydration catalyst that is liquid or soluble in a liquid reaction mixture under the reaction conditions is used in an amount of from 0.001 to 0.5 mole per 1 mole of the alicyclic alcohol.

5. The method for producing a cyclic olefin compound, according to claim 1, wherein the alicyclic alcohol having two or more hydroxylated cyclohexane rings per molecule is a compound represented by following Formula (1a):

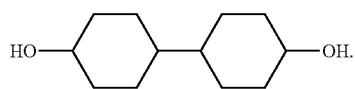
(1a)

6. The method for producing a cyclic olefin compound, according to claim 1, wherein the alicyclic alcohol having two or more hydroxylated cyclohexane rings per molecule is a compound represented by following Formula (1b):

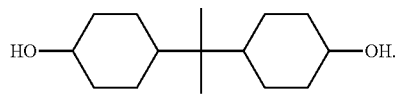
(1b)

7. The method for producing a cyclic olefin compound, according to claim 1, wherein the alicyclic alcohol having two or more hydroxylated cyclohexane rings per molecule is a compound represented by following Formula (1c):

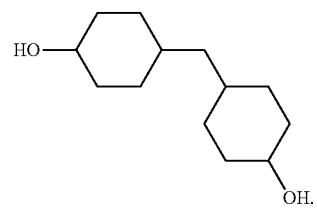
(1c)

8. The method for producing a cyclic olefin compound, according to claim 1, wherein the organic solvent is at least one selected from the group consisting of cumene, pseudocumene and undecane.

* * * * *